(12) United States Patent
Kikuchi et al.

(10) Patent No.: US 11,244,478 B2
(45) Date of Patent: Feb. 8, 2022

(54) MEDICAL IMAGE PROCESSING DEVICE, SYSTEM, METHOD, AND PROGRAM

(71) Applicant: SONY CORPORATION, Tokyo (JP)

(72) Inventors: Daisuke Kikuchi, Kanagawa (JP);
Takami Mizukura, Kanagawa (JP);
Yasuaki Takahashi, Kanagawa (JP);
Koji Kashima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 44 days.

(21) Appl. No.: 16/076,784

(22) PCT Filed: Jan. 10, 2017

(86) PCT No.: PCT/JP2017/000424
§ 371 (c)(1),
(2) Date: Aug. 9, 2018

(87) PCT Pub. No.: WO2017/149932
PCT Pub. Date: Sep. 8, 2017

(65) Prior Publication Data
US 2019/0051022 A1 Feb. 14, 2019

(30) Foreign Application Priority Data
Mar. 3, 2016 (JP) .............................. JP2016-040760

(51) Int. Cl.
*G06T 11/00* (2006.01)
*A61B 1/04* (2006.01)
(Continued)

(52) U.S. Cl.
CPC ........ *G06T 11/001* (2013.01); *A61B 1/00009* (2013.01); *A61B 1/04* (2013.01);
(Continued)

(58) Field of Classification Search
CPC .... H04N 5/2355; H04N 9/045; H04N 5/2352; H04N 13/25; H04N 9/735;
(Continued)

(56) References Cited

U.S. PATENT DOCUMENTS 3,748,981 A * 7/1973 Staes .................... G01J 1/42
430/359
4,111,548 A * 9/1978 Pechev ................ G03B 27/547
355/30

(Continued)

FOREIGN PATENT DOCUMENTS

JP 2008-276482 A 11/2008
JP 2011-232370 A 11/2011
(Continued)

OTHER PUBLICATIONS

International Search Report dated Feb. 28, 2017 in PCT/JP2017/000424, 2 pages.

*Primary Examiner* — Charles L Beard
(74) *Attorney, Agent, or Firm* — Xsensus LLP

(57) ABSTRACT

[Object] To reduce a risk that a tone of a specific color component of a subject to be observed in medical operation is defective.
[Solution] There is provided a medical image processing device including: a signal acquisition unit configured to acquire a first specific component image signal with a first exposure for a specific color component, a second specific component image signal with a second exposure different from the first exposure for the specific color component, and two non-specific component image signals corresponding to two color components different from the specific color component; a combination unit configured to generate a specific component combination image signal by combining the first specific component image signal and the second specific component image signal by using a weight based on (Continued)

an intensity of the specific color component; and a color image generation unit configured to generate a color image signal on a basis of the specific component combination image signal generated by the combination unit and the two non-specific component image signals.

19 Claims, 17 Drawing Sheets

(51) Int. Cl.
 *A61B 1/00* (2006.01)
 *G06T 7/90* (2017.01)
 *G16H 30/40* (2018.01)
 *A61B 1/06* (2006.01)

(52) U.S. Cl.
 CPC .............. *G06T 7/90* (2017.01); *G16H 30/40* (2018.01); *A61B 1/043* (2013.01); *A61B 1/0638* (2013.01); *G06T 2210/41* (2013.01)

(58) Field of Classification Search
 CPC ......... H04N 5/35554; H04N 2209/045; G09G 5/026; G09G 5/377; G09G 2320/02; A61B 1/0638; A61B 1/00006; A61B 1/00009; A61B 1/00057; A61B 1/04; A61B 1/043; G06T 2207/10068; G06T 2207/10012; G06T 2207/10021; G06T 2207/10121; G06T 2207/10124; G06T 2207/10141; G06T 2207/10144; G06T 7/85; G06T 2210/41; G06T 11/001; G06T 7/90; G16H 30/40
 See application file for complete search history.

(56) References Cited

U.S. PATENT DOCUMENTS

| | | | | |
|---|---|---|---|---|
| 4,565,441 A * | 1/1986 | Evans | G03B 27/547 | 355/37 |
| 4,667,228 A * | 5/1987 | Kawamura | H04N 1/4074 | 348/672 |
| 4,754,323 A * | 6/1988 | Kaji | H04N 9/0451 | 348/256 |
| 4,764,807 A * | 8/1988 | Kimura | H04N 1/508 | 346/107.2 |
| 4,774,564 A * | 9/1988 | Konishi | H04N 5/235 | 348/224.1 |
| 4,942,424 A * | 7/1990 | Terashita | G03B 27/735 | 355/38 |
| 5,042,078 A * | 8/1991 | Oshikoshi | H04N 1/6027 | 382/167 |
| 5,148,809 A * | 9/1992 | Biegeleisen-Knight | A61B 8/488 | 348/163 |
| 5,255,077 A * | 10/1993 | Yamazaki | H04N 9/735 | 348/226.1 |
| 5,260,774 A * | 11/1993 | Takayama | H04N 9/735 | 348/223.1 |
| 5,300,381 A * | 4/1994 | Buhr | H04N 1/407 | 355/32 |
| 5,422,738 A * | 6/1995 | Ishihara | H04N 1/6019 | 358/500 |
| 5,461,457 A * | 10/1995 | Nakamura | G03B 27/735 | 355/38 |
| 5,528,339 A * | 6/1996 | Buhr | H04N 1/4072 | 355/32 |
| 5,563,666 A * | 10/1996 | Suzuki | H04N 9/68 | 348/645 |
| 5,579,132 A * | 11/1996 | Takahashi | H04N 1/6011 | 358/519 |
| 5,589,879 A * | 12/1996 | Saito | H04N 9/735 | 348/223.1 |
| 5,619,280 A * | 4/1997 | Yamashita | H04N 9/67 | 348/645 |
| 5,631,748 A * | 5/1997 | Harrington | H04N 1/52 | 347/251 |
| 5,657,094 A * | 8/1997 | Moriwake | H04N 9/74 | 348/578 |
| 5,687,407 A * | 11/1997 | Iwasaki | G03B 7/28 | 348/E5.035 |
| 5,729,624 A * | 3/1998 | Tanioka | H04N 1/52 | 382/162 |
| 5,802,214 A * | 9/1998 | Eschbach | H04N 1/6027 | 382/254 |
| 5,812,178 A * | 9/1998 | Yamaguchi | H04N 1/6027 | 347/232 |
| 5,817,440 A * | 10/1998 | Hirai | G02B 5/223 | 430/7 |
| 5,828,362 A * | 10/1998 | Takahashi | H04N 9/12 | 345/589 |
| 5,891,607 A * | 4/1999 | Brewer | G03C 7/3041 | 430/383 |
| 5,926,560 A * | 7/1999 | Ichinose | H04N 1/40056 | 382/162 |
| 5,949,482 A * | 9/1999 | Kawa | H04N 9/68 | 348/256 |
| 5,953,058 A * | 9/1999 | Hanagata | H04N 9/735 | 348/223.1 |
| 5,991,056 A * | 11/1999 | Takamori | H04N 1/6025 | 358/518 |
| 6,011,636 A * | 1/2000 | Tanaka | H04N 1/4076 | 358/527 |
| 6,023,524 A * | 2/2000 | Yamaguchi | G03B 27/735 | 382/162 |
| 6,075,562 A * | 6/2000 | Sakaguchi | H04N 1/407 | 348/223.1 |
| 6,111,607 A * | 8/2000 | Kameyama | G06T 5/009 | 348/255 |
| 6,111,911 A * | 8/2000 | Sanderford, Jr. | H04B 1/707 | 375/141 |
| 6,115,148 A * | 9/2000 | Imai | H04N 1/46 | 358/500 |
| 6,184,453 B1 * | 2/2001 | Izumisawa | G10H 1/125 | 84/604 |
| 6,190,847 B1 * | 2/2001 | Sowinski | G03C 7/30 | 430/544 |
| 6,191,874 B1 * | 2/2001 | Yamada | H04N 1/6022 | 358/518 |
| 6,271,891 B1 * | 8/2001 | Ogawa | H04N 9/69 | 348/254 |
| 6,337,692 B1 * | 1/2002 | Rai | G06T 5/008 | 345/589 |
| 6,372,418 B1 * | 4/2002 | Gisser | G03C 7/22 | 430/505 |
| 6,603,452 B1 * | 8/2003 | Serita | G09G 3/3611 | 345/88 |
| 6,618,502 B1 * | 9/2003 | Okada | H04N 5/235 | 348/225.1 |
| 6,643,397 B1 * | 11/2003 | Kanamori | H04N 1/4074 | 358/522 |
| 6,654,055 B1 * | 11/2003 | Park | H04N 1/6086 | 348/242 |
| 6,747,694 B1 * | 6/2004 | Nishikawa | H04N 5/2355 | 348/229.1 |
| 6,809,714 B1 * | 10/2004 | Yamauchi | G09G 5/02 | 345/88 |
| 6,844,941 B1 * | 1/2005 | Sharma | H04N 1/52 | 358/1.9 |
| 7,324,143 B1 * | 1/2008 | Pelz | G06T 5/002 | 348/241 |
| 7,456,384 B2 * | 11/2008 | Toda | H01L 27/14685 | 250/226 |
| 7,492,391 B1 * | 2/2009 | Kaplinsky | G06T 5/50 | 348/211.3 |
| 7,570,290 B2 * | 8/2009 | Yokota | H04N 3/1562 | 348/275 |
| 7,889,216 B2 * | 2/2011 | Moriya | G09G 3/3607 | 345/694 |

(56) References Cited

U.S. PATENT DOCUMENTS

| | | | | |
|---|---|---|---|---|
| 8,335,426 B2* | 12/2012 | Isobe | G11B 27/034 | 386/337 |
| 8,824,752 B1* | 9/2014 | Fonte | A61B 6/504 | 382/126 |
| 9,204,020 B2* | 12/2015 | Kawai | H04N 13/218 | |
| 9,247,153 B2* | 1/2016 | Umezu | H04N 5/23264 | |
| 9,426,438 B2* | 8/2016 | Furukawa | H04N 5/2355 | |
| 9,467,632 B1* | 10/2016 | Chen | H04N 5/2353 | |
| 9,509,917 B2* | 11/2016 | Blanquart | H04N 5/35554 | |
| 9,516,239 B2* | 12/2016 | Blanquart | H04N 9/646 | |
| 9,531,958 B2* | 12/2016 | Kasai | H04N 5/2353 | |
| 9,538,076 B2* | 1/2017 | Kim | G06T 5/006 | |
| 9,787,909 B1* | 10/2017 | Hawkins | H04N 5/35581 | |
| 9,848,137 B2* | 12/2017 | Hizi | H04N 5/3535 | |
| 9,894,304 B1* | 2/2018 | Smith | G06T 3/4015 | |
| 9,939,782 B2* | 4/2018 | Nakamura | G03H 1/28 | |
| 10,085,002 B2* | 9/2018 | Cho | H04N 13/139 | |
| 10,412,356 B2* | 9/2019 | Eto | G06T 1/00 | |
| 10,462,390 B2* | 10/2019 | Sugiyama | H04N 5/378 | |
| 10,645,294 B1* | 5/2020 | Manzari | H04N 5/232933 | |
| 10,788,676 B2* | 9/2020 | Nagae | A61B 1/00186 | |
| 10,819,927 B1* | 10/2020 | Mikes | H04N 5/378 | |
| 10,835,104 B2* | 11/2020 | Ioka | G06T 3/4015 | |
| 2002/0036696 A1* | 3/2002 | Takemoto | H04N 1/60 | 348/211.6 |
| 2002/0089596 A1* | 7/2002 | Suda | H04N 9/045 | 348/302 |
| 2002/0135750 A1* | 9/2002 | Arndt | G01P 5/001 | 356/28.5 |
| 2002/0171663 A1* | 11/2002 | Kobayashi | H04N 1/6027 | 345/600 |
| 2003/0058349 A1* | 3/2003 | Takemoto | H04N 1/6086 | 348/222.1 |
| 2004/0012341 A1* | 1/2004 | Hyuga | H04N 1/504 | 315/169.3 |
| 2004/0017379 A1* | 1/2004 | Ajito | H04N 1/6011 | 345/600 |
| 2005/0001986 A1* | 1/2005 | Matsuda | G09G 5/02 | 353/31 |
| 2005/0190200 A1* | 9/2005 | Arazaki | G06T 3/4015 | 345/600 |
| 2005/0280850 A1* | 12/2005 | Kim | H04N 9/3182 | 358/1.9 |
| 2006/0050033 A1* | 3/2006 | Asao | G09G 3/3607 | 345/88 |
| 2006/0109358 A1* | 5/2006 | Song | H04N 9/04561 | 348/275 |
| 2006/0245014 A1* | 11/2006 | Haneda | H04N 1/4072 | 358/512 |
| 2007/0024879 A1* | 2/2007 | Hamilton, Jr. | H04N 9/045 | 358/1.9 |
| 2007/0024931 A1* | 2/2007 | Compton | H04N 9/045 | 358/512 |
| 2007/0046807 A1* | 3/2007 | Hamilton, Jr. | H04N 5/235 | 348/362 |
| 2007/0167801 A1* | 7/2007 | Webler | A61B 8/445 | 600/459 |
| 2007/0236617 A1* | 10/2007 | Lippey | H04N 13/334 | 349/5 |
| 2008/0084524 A1* | 4/2008 | Inuzuka | G09G 3/3413 | 349/108 |
| 2008/0094493 A1* | 4/2008 | Igarashi | H04N 5/202 | 348/254 |
| 2008/0100612 A1* | 5/2008 | Dastmalchi | A61B 3/0058 | 345/418 |
| 2008/0100644 A1* | 5/2008 | Chiang | G09G 3/20 | 345/690 |
| 2008/0112611 A1* | 5/2008 | Sasaki | H04N 1/644 | 382/162 |
| 2008/0267522 A1* | 10/2008 | Kobayashi | G06T 5/009 | 382/254 |
| 2008/0284880 A1* | 11/2008 | Numata | H04N 5/217 | 348/241 |
| 2009/0027487 A1* | 1/2009 | Misawa | H04N 13/10 | 348/51 |
| 2009/0033964 A1* | 2/2009 | Kubota | H04N 1/38 | 358/1.9 |
| 2009/0034005 A1* | 2/2009 | Gotoh | H04N 1/40062 | 358/3.06 |
| 2009/0046453 A1* | 2/2009 | Kramer | H05B 45/22 | 362/231 |
| 2009/0059048 A1* | 3/2009 | Luo | H04N 5/347 | 348/308 |
| 2009/0238455 A1* | 9/2009 | Kasahara | H04N 9/04515 | 382/167 |
| 2009/0278982 A1* | 11/2009 | Imai | H04N 9/67 | 348/453 |
| 2009/0290052 A1* | 11/2009 | Liu | H04N 9/045 | 348/277 |
| 2009/0323026 A1* | 12/2009 | Mizushima | G03B 21/208 | 353/31 |
| 2010/0002093 A1* | 1/2010 | Arai | H04N 5/23219 | 348/229.1 |
| 2010/0013866 A1* | 1/2010 | Okabe | G02F 1/1336 | 345/690 |
| 2010/0013952 A1* | 1/2010 | Kwon | H04N 9/735 | 348/223.1 |
| 2010/0020205 A1* | 1/2010 | Ishida | G06T 5/008 | 348/241 |
| 2010/0066858 A1* | 3/2010 | Asoma | H04N 5/2353 | 348/229.1 |
| 2010/0074553 A1* | 3/2010 | Choi | G09G 3/36 | 382/274 |
| 2010/0097493 A1* | 4/2010 | Asoma | H04N 5/235 | 348/229.1 |
| 2010/0157112 A1* | 6/2010 | Miyagi | H04N 5/202 | 348/242 |
| 2010/0277631 A1* | 11/2010 | Sugiyama | H04N 5/35581 | 348/297 |
| 2010/0283866 A1* | 11/2010 | Numata | H04N 9/735 | 348/223.1 |
| 2010/0315530 A1* | 12/2010 | Lee | H04N 5/243 | 348/223.1 |
| 2010/0315534 A1* | 12/2010 | Azuma | H04N 9/045 | 348/234 |
| 2011/0018970 A1* | 1/2011 | Wakabayashi | H04N 5/232123 | 348/47 |
| 2011/0050918 A1* | 3/2011 | Tachi | H04N 9/04559 | 348/208.4 |
| 2011/0137156 A1* | 6/2011 | Razzaque | A61B 18/1477 | 600/424 |
| 2011/0181760 A1* | 7/2011 | Horie | H04N 9/04515 | 348/242 |
| 2011/0242368 A1* | 10/2011 | Haneda | H04N 5/2355 | 348/239 |
| 2011/0279705 A1* | 11/2011 | Kuang | H04N 5/343 | 348/229.1 |
| 2011/0279716 A1* | 11/2011 | Shintani | H04N 9/04557 | 348/272 |
| 2012/0026210 A1* | 2/2012 | Yano | G09G 3/3607 | 345/690 |
| 2012/0038758 A1* | 2/2012 | Khassanov | H04N 13/398 | 348/60 |
| 2012/0044394 A1* | 2/2012 | Komiya | H04N 9/0451 | 348/266 |
| 2012/0062616 A1* | 3/2012 | Nose | G02F 1/13718 | 345/690 |
| 2012/0062746 A1* | 3/2012 | Otsuka | H04N 5/2353 | 348/148 |
| 2012/0127337 A1* | 5/2012 | Okada | H04N 5/23232 | 348/223.1 |
| 2012/0133670 A1* | 5/2012 | Kim | G09G 5/02 | 345/593 |
| 2012/0140182 A1* | 6/2012 | Relke | H04N 13/312 | 353/7 |
| 2012/0169842 A1* | 7/2012 | Chuang | G08B 13/19619 | 348/39 |

(56) References Cited

U.S. PATENT DOCUMENTS

| | | | |
|---|---|---|---|
| 2012/0218426 A1* | 8/2012 | Kaizu | H04N 5/35554 348/208.4 |
| 2012/0287156 A1* | 11/2012 | Tsujita | G01S 7/52071 345/629 |
| 2012/0293531 A1* | 11/2012 | Wang | G09G 3/2003 345/589 |
| 2012/0321208 A1* | 12/2012 | Uematsu | H04N 19/137 382/238 |
| 2013/0051700 A1* | 2/2013 | Jo | G06T 5/003 382/284 |
| 2013/0057547 A1* | 3/2013 | Hwang | G06T 7/75 345/420 |
| 2013/0057724 A1* | 3/2013 | Miyahara | H04N 9/04557 348/223.1 |
| 2013/0093783 A1* | 4/2013 | Sullivan | G06T 11/001 345/601 |
| 2013/0120615 A1* | 5/2013 | Hirooka | H04N 5/2355 348/239 |
| 2013/0128083 A1* | 5/2013 | Liu | H04N 5/2355 348/262 |
| 2013/0216130 A1* | 8/2013 | Saito | H04N 9/04555 382/165 |
| 2013/0265462 A1* | 10/2013 | Kano | H04N 9/735 348/223.1 |
| 2014/0027613 A1* | 1/2014 | Smith | H01L 27/14621 250/208.1 |
| 2014/0063300 A1* | 3/2014 | Lin | H04N 9/045 348/277 |
| 2014/0160260 A1* | 6/2014 | Blanquart | H04N 5/2256 348/68 |
| 2014/0160318 A1* | 6/2014 | Blanquart | A61B 1/045 348/234 |
| 2014/0160326 A1* | 6/2014 | Black | H04N 9/045 348/262 |
| 2014/0176799 A1* | 6/2014 | Kondo | H04N 17/004 348/575 |
| 2014/0192250 A1* | 7/2014 | Mitsunaga | H04N 5/37457 348/349 |
| 2014/0212014 A1* | 7/2014 | Kim | G06T 3/0068 382/131 |
| 2014/0232901 A1* | 8/2014 | Furuta | H04N 9/0451 348/223.1 |
| 2014/0267914 A1* | 9/2014 | Sfaradi | G06T 5/007 348/571 |
| 2014/0300753 A1* | 10/2014 | Yin | G01J 3/502 348/187 |
| 2014/0307098 A1* | 10/2014 | Kang | H04N 17/002 348/164 |
| 2014/0307131 A1* | 10/2014 | Tanaka | H04N 9/04515 348/273 |
| 2014/0313369 A1* | 10/2014 | Kageyama | G06T 5/50 348/223.1 |
| 2015/0029358 A1* | 1/2015 | Kaizu | G06T 3/4015 348/223.1 |
| 2015/0042775 A1* | 2/2015 | Zhao | H04N 9/04557 348/71 |
| 2015/0042848 A1* | 2/2015 | Furukawa | H04N 5/2355 348/242 |
| 2015/0062368 A1* | 3/2015 | Li | H04N 5/2355 348/222.1 |
| 2015/0109491 A1* | 4/2015 | Hayashi | H04N 9/04557 348/273 |
| 2015/0109492 A1* | 4/2015 | Hayashi | H01L 27/14621 348/277 |
| 2015/0109493 A1* | 4/2015 | Hayashi | H04N 9/04515 348/277 |
| 2015/0109495 A1* | 4/2015 | Tanaka | H04N 9/04557 348/277 |
| 2015/0109497 A1* | 4/2015 | Tanaka | H04N 9/30 348/280 |
| 2015/0116554 A1* | 4/2015 | Tanaka | H01L 27/14645 348/277 |
| 2015/0116555 A1* | 4/2015 | Hayashi | H04N 9/04515 348/280 |
| 2015/0150526 A1* | 6/2015 | Ohishi | A61B 6/469 378/62 |
| 2015/0172618 A1* | 6/2015 | Takahashi | H04N 9/04555 348/164 |
| 2015/0172622 A1* | 6/2015 | Yoon | H04N 13/122 345/694 |
| 2015/0221105 A1* | 8/2015 | Tripathi | G06F 19/00 382/131 |
| 2015/0237273 A1* | 8/2015 | Sawadaishi | H04N 9/07 348/234 |
| 2015/0244923 A1* | 8/2015 | Lee | H04N 9/045 348/234 |
| 2015/0254852 A1* | 9/2015 | Yamato | A61B 6/5288 345/634 |
| 2015/0288950 A1* | 10/2015 | Zhang | H04N 5/33 348/47 |
| 2015/0289848 A1* | 10/2015 | Hwang | A61B 6/5288 600/411 |
| 2015/0310650 A1* | 10/2015 | Lu | G06T 5/009 324/322 |
| 2015/0312461 A1* | 10/2015 | Kim | H04N 5/378 348/308 |
| 2015/0332461 A1* | 11/2015 | Kim | A61B 6/4417 382/131 |
| 2015/0334276 A1* | 11/2015 | Ecker | H04N 5/341 348/76 |
| 2015/0348242 A1* | 12/2015 | Molgaard | G06T 5/002 348/241 |
| 2015/0350509 A1* | 12/2015 | Tico | H04N 5/2355 348/362 |
| 2015/0366444 A1* | 12/2015 | Morimoto | A61B 5/1459 600/339 |
| 2016/0027184 A1* | 1/2016 | Courtney | G06T 15/08 345/424 |
| 2016/0027206 A1* | 1/2016 | Beach | G06T 15/506 382/128 |
| 2016/0037044 A1* | 2/2016 | Motta | G06T 3/4015 348/221.1 |
| 2016/0117823 A1* | 4/2016 | Isaacs | A61B 6/4441 715/863 |
| 2016/0119532 A1* | 4/2016 | Chen | H04N 5/23222 348/211.2 |
| 2016/0142645 A1* | 5/2016 | Shionoya | H04N 5/379 348/218.1 |
| 2016/0163101 A1* | 6/2016 | Jang | A61B 6/032 382/131 |
| 2016/0173751 A1* | 6/2016 | Nakata | H04N 5/35554 348/362 |
| 2016/0173752 A1* | 6/2016 | Caviedes | H04N 5/23229 348/207.11 |
| 2016/0191887 A1* | 6/2016 | Casas | H04N 13/279 348/47 |
| 2016/0198103 A1* | 7/2016 | Tanaka | G03B 15/05 348/164 |
| 2016/0205359 A1* | 7/2016 | Hirota | H04N 9/045 348/280 |
| 2016/0253800 A1* | 9/2016 | Gurevich | A61B 5/445 382/128 |
| 2016/0328848 A1* | 11/2016 | Andre | H04N 1/482 |
| 2016/0350960 A1* | 12/2016 | Yi | G06T 15/06 |
| 2017/0008174 A1* | 1/2017 | Rosen | B25J 9/1694 |
| 2017/0018239 A1* | 1/2017 | Chen | G06F 3/041 |
| 2017/0034639 A1* | 2/2017 | Chon | H04S 3/008 |
| 2017/0116933 A1* | 4/2017 | Xu | G09G 3/3648 |
| 2017/0215713 A1* | 8/2017 | Takahashi | A61B 1/045 |
| 2017/0230624 A1* | 8/2017 | Hanawa | A61B 1/05 |
| 2017/0237887 A1* | 8/2017 | Tanaka | G03B 15/05 348/164 |
| 2017/0238791 A1* | 8/2017 | Kagawa | A61B 1/0638 |
| 2017/0257548 A1* | 9/2017 | Tamai | H04N 13/25 |
| 2017/0301069 A1* | 10/2017 | Sato | G06T 1/20 |
| 2017/0339353 A1* | 11/2017 | Banachowicz | H04N 5/3696 |
| 2017/0339385 A1* | 11/2017 | Usui | H04N 9/077 |
| 2017/0347086 A1* | 11/2017 | Watanabe | H04N 13/25 |

(56) References Cited

U.S. PATENT DOCUMENTS

| | | | |
|---|---|---|---|
| 2017/0353678 A1* | 12/2017 | Ogushi | H04N 5/2353 |
| 2017/0370846 A1* | 12/2017 | Shelley, Jr. | G01N 21/6456 |
| 2017/0374263 A1* | 12/2017 | Somayaji | H04N 5/2351 |
| 2018/0021004 A1* | 1/2018 | Ishii | A61B 6/54 |
| | | | 378/62 |
| 2018/0027222 A1* | 1/2018 | Ogasawara | H04N 5/225 |
| | | | 348/175 |
| 2018/0041724 A1* | 2/2018 | Kim | H04N 5/355 |
| 2018/0049632 A1* | 2/2018 | Shida | A61B 1/00045 |
| 2018/0092616 A1* | 4/2018 | Sakaguchi | G06T 7/0016 |
| 2018/0108169 A1* | 4/2018 | Miller | G06T 15/06 |
| 2018/0152634 A1* | 5/2018 | Tang | H04N 9/735 |
| 2018/0152664 A1* | 5/2018 | Urabe | H04N 7/0127 |
| 2018/0153386 A1* | 6/2018 | Omori | A61B 1/00186 |
| 2018/0159624 A1* | 6/2018 | Jang | H04N 5/3532 |
| 2018/0212646 A1* | 7/2018 | Hannebauer | H04J 13/10 |
| 2018/0234591 A1* | 8/2018 | Ochiai | H04N 1/60 |
| 2018/0263479 A1* | 9/2018 | Ito | A61B 1/0646 |
| 2018/0270462 A1* | 9/2018 | Otsubo | G02B 5/201 |
| 2018/0278913 A1* | 9/2018 | Attar | H04N 13/257 |
| 2018/0324344 A1* | 11/2018 | Kinoshita | H04N 5/2355 |
| 2018/0330476 A1* | 11/2018 | Omori | H04N 5/357 |
| 2018/0341804 A1* | 11/2018 | Takayama | G06K 9/00234 |
| 2018/0343404 A1* | 11/2018 | Hwang | H04N 5/3745 |
| 2018/0368783 A1* | 12/2018 | Pohl | G06K 9/6204 |
| 2019/0018231 A1* | 1/2019 | Dixon | G02B 21/002 |
| 2019/0027183 A1* | 1/2019 | Price | H01L 27/14643 |
| 2019/0037115 A1* | 1/2019 | Yasugi | G01J 3/46 |
| 2019/0068929 A1* | 2/2019 | Sato | H04N 5/2353 |
| 2019/0087961 A1* | 3/2019 | Tian | B60T 7/12 |
| 2019/0109994 A1* | 4/2019 | Kikuchi | H04N 5/232122 |
| 2019/0149713 A1* | 5/2019 | Blanquart | H04N 9/045 |
| | | | 348/266 |
| 2019/0156516 A1* | 5/2019 | Nikkanen | G06T 7/90 |
| 2019/0170585 A1* | 6/2019 | Okada | G06K 9/4652 |
| 2019/0206344 A1* | 7/2019 | Kang | G09G 3/3426 |
| 2019/0378258 A1* | 12/2019 | Fan | H04N 5/33 |
| 2020/0020285 A1* | 1/2020 | Shan | G09G 3/3607 |
| 2020/0020286 A1* | 1/2020 | Shan | G09G 3/3607 |
| 2020/0260941 A1* | 8/2020 | Kubo | A61B 1/0005 |
| 2021/0020120 A1* | 1/2021 | Kang | G09G 3/3413 |
| 2021/0160415 A1* | 5/2021 | Han | H04N 5/2351 |
| 2021/0173246 A1* | 6/2021 | Du | G09G 3/3607 |
| 2021/0183323 A1* | 6/2021 | He | G09G 3/3607 |
| 2021/0210031 A1* | 7/2021 | Kang | G09G 3/3413 |
| 2021/0255286 A1* | 8/2021 | Nagase | H04N 5/232 |

FOREIGN PATENT DOCUMENTS

| | | |
|---|---|---|
| JP | 2013-162347 A | 8/2013 |
| JP | 2014-230708 A | 12/2014 |
| JP | 2015-41890 A | 3/2015 |
| WO | WO 2012/004928 A1 | 1/2012 |

* cited by examiner

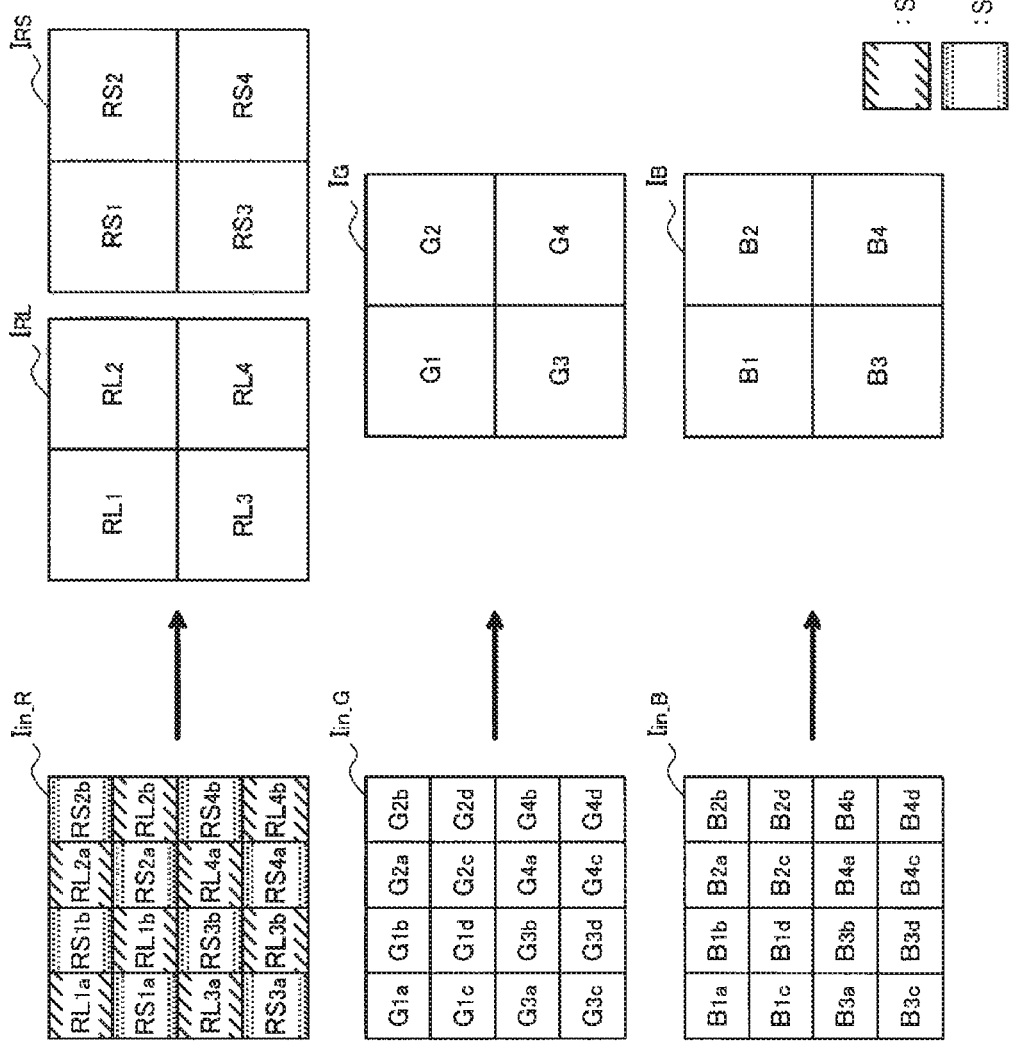

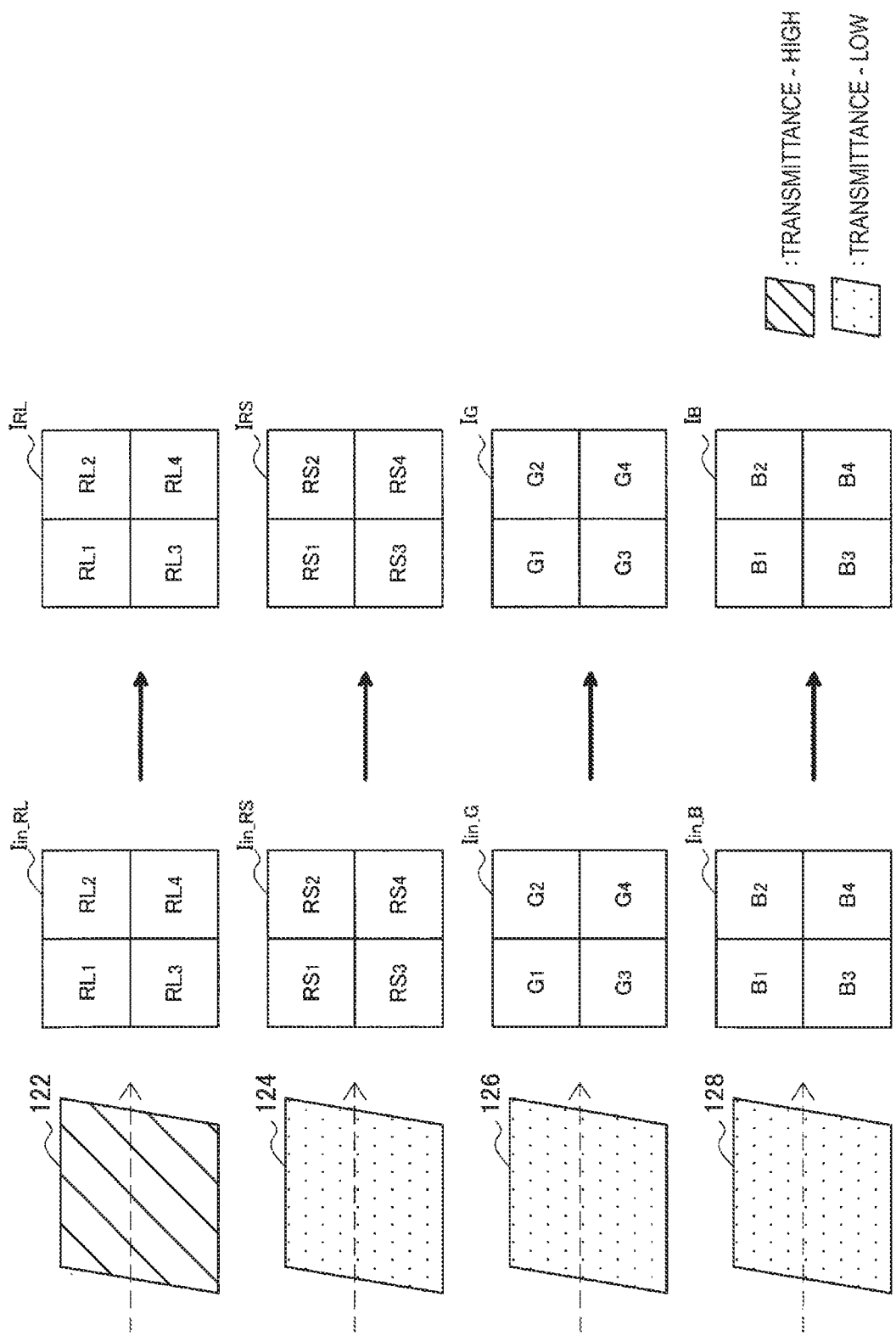

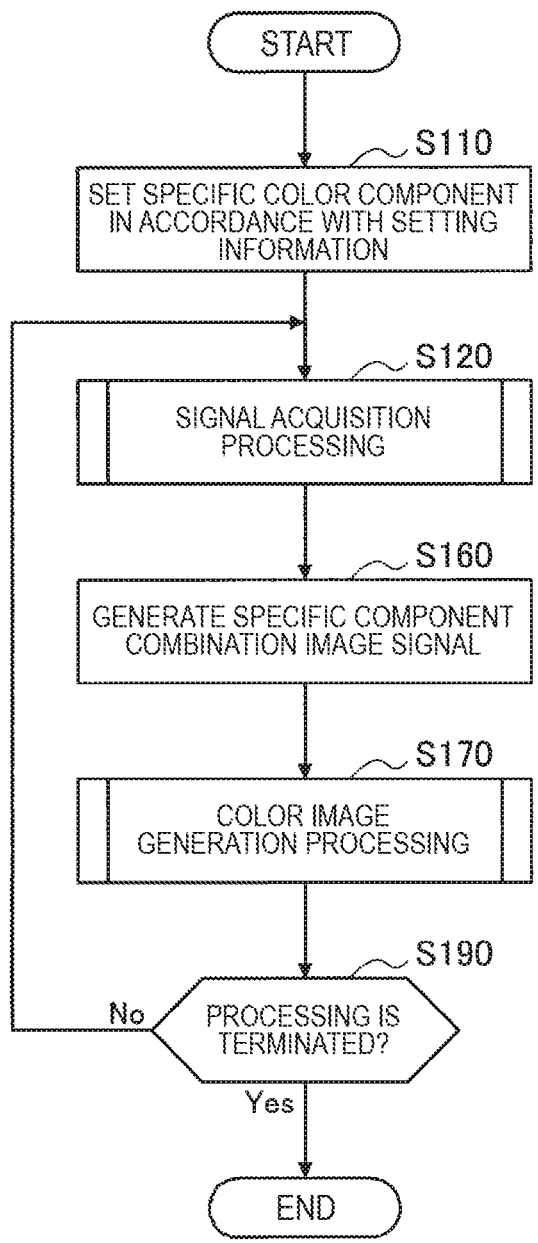

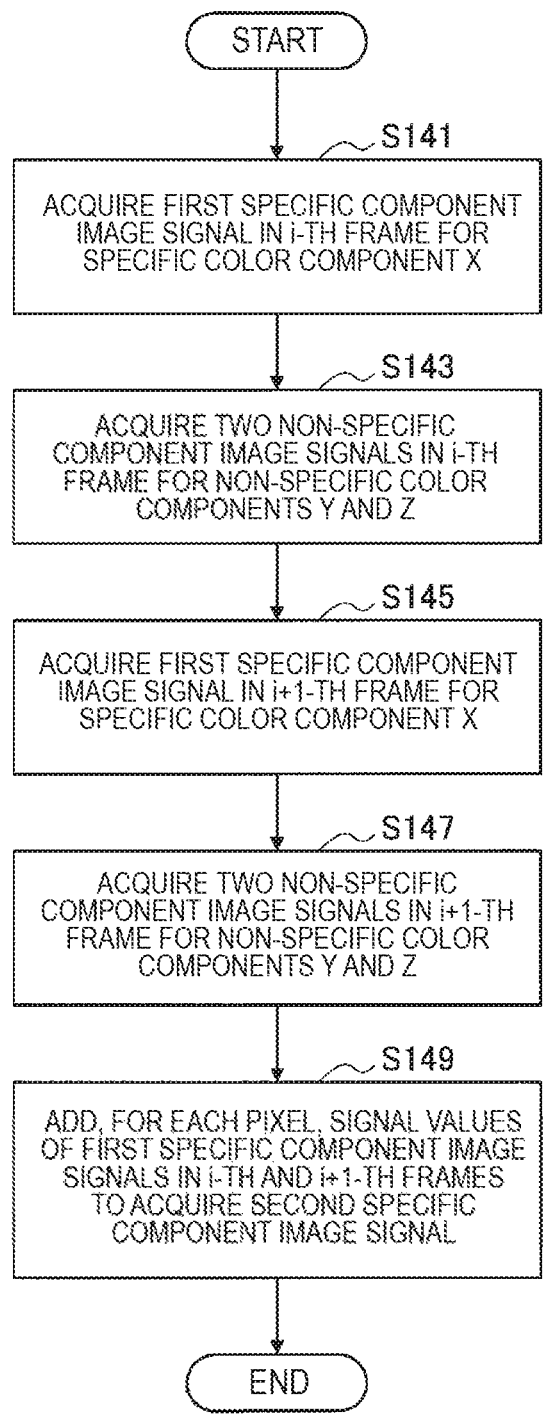

MEDICAL IMAGE PROCESSING DEVICE, SYSTEM, METHOD, AND PROGRAM

TECHNICAL FIELD

The present disclosure relates to a medical image processing device, system, method, and program.

BACKGROUND ART

In recent years, medical observation devices such as endoscopes and microscopes have been widely used in medical scenes. The medical observation devices include not only a device capable of optically observing a subject but also a device that causes a display unit to electronically display an image of the subject captured by an imaging unit (camera). For example, in endoscopic surgery or microsurgery, a practitioner performs various types of operation while observing an affected part or a surgical instrument through an image that is electronically displayed. A capsule endoscope is mainly used for examination or diagnosis and captures an image of an objective organ inside a body of a subject.

In a case where a captured image is displayed for the medical operation exemplified above, a subject needs to be displayed as clearly as possible in the displayed image. However, actually, a defect of visual information called clipped whites or clipped blacks occurs in many cases due to restriction of a dynamic range of a pixel value. Patent Literature 1 proposes a mechanism that variably controls a peak position of a light distribution of illumination light emitted toward a visual field in order to prevent such clipped whites or clipped blacks and provide a natural image.

CITATION LIST

Patent Literature

Patent Literature 1: JP 2014-230708A

DISCLOSURE OF INVENTION

Technical Problem

However, an existing technology for preventing clipped whites or clipped blacks does not consider an imbalance between tones of respective color components in a subject observed in medical operation. For example, in a case where the inside of a living body is observed, magnitude of a red component may strongly influence a tone of a subject. Further, in special light observation (e.g., fluorescence observation, observation using staining, or the like), specific color other than red is particularly meaningful in a tone of a subject in some cases. In those cases, when dynamic ranges of a plurality of color components are attempted to be uniformly adjusted, a dynamic range of a specific color component does not become optimal as a result, and a tone to be observed may be defective.

An object of a technology of the present disclosure is to solve or at least reduce such a disadvantage of the existing technology.

Solution to Problem

According to the present disclosure, there is provided a medical image processing device including: a signal acquisition unit configured to acquire a first specific component image signal with a first exposure for a specific color component, a second specific component image signal with a second exposure different from the first exposure for the specific color component, and two non-specific component image signals corresponding to two color components different from the specific color component; a combination unit configured to generate a specific component combination image signal by combining the first specific component image signal and the second specific component image signal by using a weight based on an intensity of the specific color component; and a color image generation unit configured to generate a color image signal on a basis of the specific component combination image signal generated by the combination unit and the two non-specific component image signals.

In addition, according to the present disclosure, there is provided a medical image processing system including: an imaging device configured to capture an image of a subject; and an image processing device configured to generate a color image signal by processing one or more image signals acquired from the imaging device. The image processing device includes a signal acquisition unit configured to acquire a first specific component image signal with a first exposure for a specific color component, a second specific component image signal with a second exposure different from the first exposure for the specific color component, and two non-specific component image signals corresponding to two color components different from the specific color component, a combination unit configured to generate a specific component combination image signal by combining the first specific component image signal and the second specific component image signal by using a weight based on an intensity of the specific color component, and a color image generation unit configured to generate a color image signal on a basis of the specific component combination image signal generated by the combination unit and the two non-specific component image signals.

In addition, according to the present disclosure, there is provided a medical image processing method including: acquiring a first specific component image signal with a first exposure for a specific color component; acquiring a second specific component image signal with a second exposure different from the first exposure for the specific color component; acquiring two non-specific component image signals corresponding to two color components different from the specific color component; generating a specific component combination image signal by combining the first specific component image signal and the second specific component image signal by using a weight based on an intensity of the specific color component; and generating a color image signal on a basis of the specific component combination image signal generated by the combination and the two non-specific component image signals.

In addition, according to the present disclosure, there is provided a program for causing a processor that controls a medical image processing device to function as: a signal acquisition unit configured to acquire a first specific component image signal with a first exposure for a specific color component, a second specific component image signal with a second exposure different from the first exposure for the specific color component, and two non-specific component image signals corresponding to two color components different from the specific color component; a combination unit configured to generate a specific component combination image signal by combining the first specific component image signal and the second specific component image signal by using a weight based on an intensity of the specific color component; and a color image generation unit configured to generate a color image signal on a basis of the specific component combination image signal generated by the combination unit and the two non-specific component image signals.

Advantageous Effects of Invention

According to the technology of the present disclosure, it is possible to reduce a risk that a tone of a specific color component of a subject to be observed in medical operation is defective and provide a clearer image of the subject than a conventional one.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 4A is an explanatory diagram for describing a first method for acquiring image signals with different exposures.

FIG. 4D is an explanatory diagram for describing a fourth method for acquiring image signals with different exposures.

FIG. 10 is a flowchart showing an example of a flow of image signal processing according to an embodiment.

FIG. 11C is a flowchart showing a third example of a more detailed flow of signal acquisition processing.

MODE(S) FOR CARRYING OUT THE INVENTION

Figure 1:
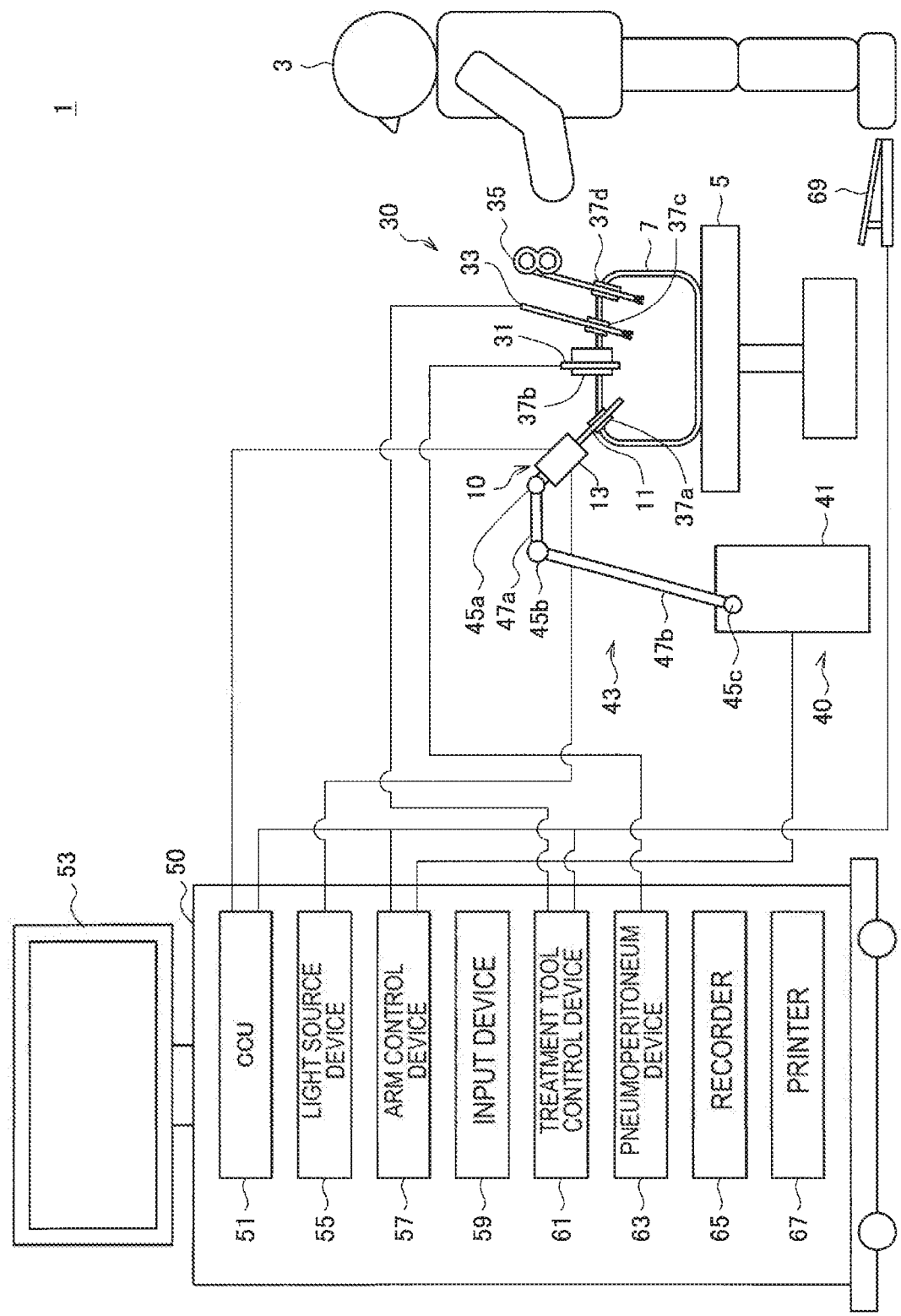
FIG. 1 is an explanatory diagram for describing a schematic configuration of a medical image processing system according to an embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, description will be provided in the following order.

1. Overview of system
2. Configuration example of device
2-1. Imaging device
2-2. Image processing device
3. Detailed examples
3-1. Acquisition of image signal
3-2. Generation of specific component combination image signal
3-3. Generation of color image
4. Flow of processing
4-1. Whole flow
4-2. Signal acquisition processing
4-3. Color image generation processing
5. Contrast sensitivity of sight of human being
6. Conclusion

1. OVERVIEW OF SYSTEM

In this section, an overview of an example system to which a technology according to the present disclosure is applicable will be described. FIG. 1 illustrates an example of a schematic configuration of a medical image processing system 1 according to an embodiment. The medical image processing system 1 is an endoscopic surgery system. In the example of FIG. 1, a practitioner (doctor) 3 performs endoscopic surgery by using the medical image processing system 1 on a patient 7 on a patient bed 5. The medical image processing system 1 includes an endoscope 10, other operation instruments 30, a support arm device 40 that supports the endoscope 10, and a cart 50 on which various devices for endoscopic surgery are mounted.

In endoscopic surgery, an abdominal wall is punctured with a plurality of cylindrical opening tools 37a to 37d called trocars, instead of being cut to open an abdomen. Then, a lens barrel 11 of the endoscope 10 and the other operation instruments 30 are inserted into a body cavity of the patient 7 through the trocars 37a to 37d. In the example of FIG. 1, a pneumoperitoneum tube 31, an energy treatment device 33, and a forceps 35 are illustrated as the other operation instruments 30. The energy treatment device 33 is used for treatment such as incision or separation of tissue or sealing of a blood vessel with a high-frequency current or ultrasonic vibration. Note that the illustrated operation instruments 30 are merely examples, and other types of operation instruments (e.g., thumb forceps, retractor, or the like) may be used.

An image of the inside of the body cavity of the patient 7 captured by the endoscope 10 is displayed by a display device 53. The practitioner 3 performs, for example, treatment such as excision of an affected part by using the energy treatment device 33 and the forceps 35 while viewing the display image in real time. Note that, although not illustrated, the pneumoperitoneum tube 31, the energy treatment device 33, and the forceps 35 are supported by a user such as the practitioner 3 or an assistant during surgery.

The support arm device 40 includes an arm portion 43 extending from a base portion 41. In the example of FIG. 1, the arm portion 43 includes joint portions 45*a*, 45*b*, and 45*c* and links 47*a* and 47*b* and supports the endoscope 10. As a result of driving the arm portion 43 under the control of an arm control device 57, a position and posture of the endoscope 10 can be controlled, and fixation of a stable position of the endoscope 10 can also be achieved.

The endoscope 10 includes the lens barrel 11 and a camera head 13 connected to a base end of the lens barrel 11. Part of the lens barrel 11, which has a certain length from a tip thereof, is inserted into the body cavity of the patient 7. In the example of FIG. 1, the endoscope 10 is configured as a so-called rigid endoscope having a rigid lens barrel 11. However, the endoscope 10 may be configured as a so-called flexible endoscope.

An opening into which an objective lens is fit is provided at the tip of the lens barrel 11. A light source device 55 is connected to the endoscope 10, and light generated by the light source device 55 is guided to the tip of the lens barrel by a light guide extended in the lens barrel 11, and an observation target in the body cavity of the patient 7 is irradiated with the light via the objective lens. Note that the endoscope 10 may be a forward-viewing endoscope, a forward-oblique viewing endoscope, or a lateral-viewing endoscope.

The camera head 13 is an imaging device including an optical system, a drive system, and an image sensor. The image sensor of the camera head 13 performs photoelectric conversion on reflected light (observation light) from an observation target, the reflected light being collected by the optical system, and generates an image signal serving as an electric signal. The generated image signal is transmitted as RAW data to a camera control unit (CCU) 51. The drive system of the camera head 13 causes the optical system in the head to be driven, thereby adjusting imaging conditions such as a magnification and a focal distance. The camera head 13 may be configured as a monocular camera or may be configured as a compound-eye camera. The camera head 13 may generate an image signal for a stereoscopic (3D display) image.

The CCU 51 includes a processor such as a central processing unit (CPU) or a graphics processing unit (GPU) and comprehensively controls operation of the endoscope 10 and the display device 53. Specifically, the CCU 51 processes an image signal acquired from the camera head 13 and generates a display image. In an embodiment, the display image generated by the CCU 51 is a color image. A series of display images can form a moving image (video). Image processing executed in the CCU 51 includes, for example, not only general processing such as development and noise reduction but also processing peculiar to the technology of the present disclosure described in detail below. The CCU 51 provides an image signal showing the display image to the display device 53. Further, the CCU 51 transmits a control signal to the camera head 13 to control drive of the camera head 13. The control signal can include, for example, information that specifies the imaging conditions described above.

The display device 53 displays an image on the basis of the input image signal under the control of the CCU 51. In a case where the endoscope 10 captures, for example, a high-resolution image such as a 4K (3840 horizontal pixels× 2160 vertical pixels) image or a 8K (7680 horizontal pixels× 4320 vertical pixels) image and/or captures an image of a stereoscopic image, a device having capabilities (high-resolution display and/or 3D display) corresponding thereto can be used as the display device 53.

The light source device 55 includes, for example, an LED, a xenon lamp, a laser light source, or a light source corresponding to a combination thereof and supplies irradiation light with which the observation target is to be irradiated to the endoscope 10 via the light guide.

The arm control device 57 includes, for example, a processor such as a CPU and operates in accordance with a predetermined program to control drive of the arm portion 43 of the support arm device 40.

An input device 59 includes one or more input interfaces that accept user input to the medical image processing system 1. The user can input various pieces of information or input various instructions to the medical image processing system 1 via the input device 59. For example, the user may input body information of a 16 patient or specific color information or surgical operation information described below via the input device 59. The specific color information can directly indicate a specific color component that is a main color component of the observation target. The surgical operation information can indicate a surgical form of surgical operation and be associated with the specific color component. Further, for example, the user inputs an instruction to drive the arm portion 43, an instruction to change the imaging conditions (the type of irradiation light, a magnification, a focal distance, and the like) in the endoscope 10, an instruction to drive the energy treatment device 33, or the like via the input device 59.

The input device 59 may treat any type of user input. For example, the input device 59 may detect physical user input via a mechanism such as a mouse, a keyboard, a switch (e.g., a foot switch 69), or a lever. The input device 59 may detect touch input via a touchscreen. The input device 59 may be achieved in the form of a wearable device such as an eyeglass-type device or a head mounted display (HMD) and may detect a line of sight or gesture of the user. Further, the input device 59 may include a microphone capable of acquiring voice of the user and may detect an audio command via the microphone.

A treatment tool control device 61 controls drive of the energy treatment device 33 for treatment such as cauterization or incision of tissue or sealing of a blood vessel. A pneumoperitoneum device 63 secures a visual field observed by using the endoscope 10 and sends gas into the body cavity via the pneumoperitoneum tube 31 in order to inflate the body cavity of the patient 7 for the purpose of securing an operational space of the practitioner. A recorder 65 records various pieces of information regarding surgical operation (e.g., one or more of body information, specific color information, surgical operation information, image information, and measurement information from a vital sensor (not illustrated)) on a recording medium. A printer 67 prints various pieces of information regarding surgical operation in some format such as text, an image, or a graph.

In such a medical image processing system 1, a subject serving as the observation target generally needs to be displayed as clearly as possible in the image displayed by the display device 53. It is important to achieve sufficient reproducibility of a tone of the subject in order that a practitioner performs treatment without mistakes or makes an accurate diagnosis. However, actually, a dynamic range of the image signal and the tone of the subject do not match, and, as a result, a defect of visual information called clipped whites or clipped blacks occurs in some cases. Although several technologies for preventing clipped whites or clipped blacks already exist, such existing technologies do not consider an imbalance between tones of respective color components in the subject serving as the observation target and, in most cases, uniformly treat a plurality of color components.

However, in a case where the inside of a living body is observed for medical operation, magnitude of a red component that is a main color component of blood and tissue may strongly influence the tone of the subject. Further, in special light observation, specific color other than red is particularly meaningful in the tone of the subject for purposes such as accurate diagnosis. In view of this, an embodiment of the technology of the present disclosure does not uniformly treat dynamic ranges of a plurality of color components but treats a specific color component as more important than the other color components and expands or adjusts a dynamic range thereof. Therefore, it is possible to obtain an optimal display image in which a defect of a tone to be observed is reduced as much as possible.

2. CONFIGURATION EXAMPLE OF DEVICE

Among the constituent elements of the medical image processing system 1 exemplified in FIG. 1, in particular, the camera head 13 functioning as an imaging device and the CCU 51 functioning as an image processing device mainly relate to capturing of an image of a subject and display of an image based on the captured image. In view of this, in this section, specific configurations of those two devices will be described in detail.

Note that, in the medical image processing system 1, those imaging device and image processing device are separately provided and are connected to each other via a signal line. However, the technology of the present disclosure is not limited to such an example. For example, a function of the image processing device described below may be mounted in a processor included in the imaging device. Further, the imaging device may record an image signal on a recording medium, and the image processing device may process the image signal read out from the recording medium (In this case, no signal line may exist between those two devices.).

[2-1. Imaging Device]

Figure 2:
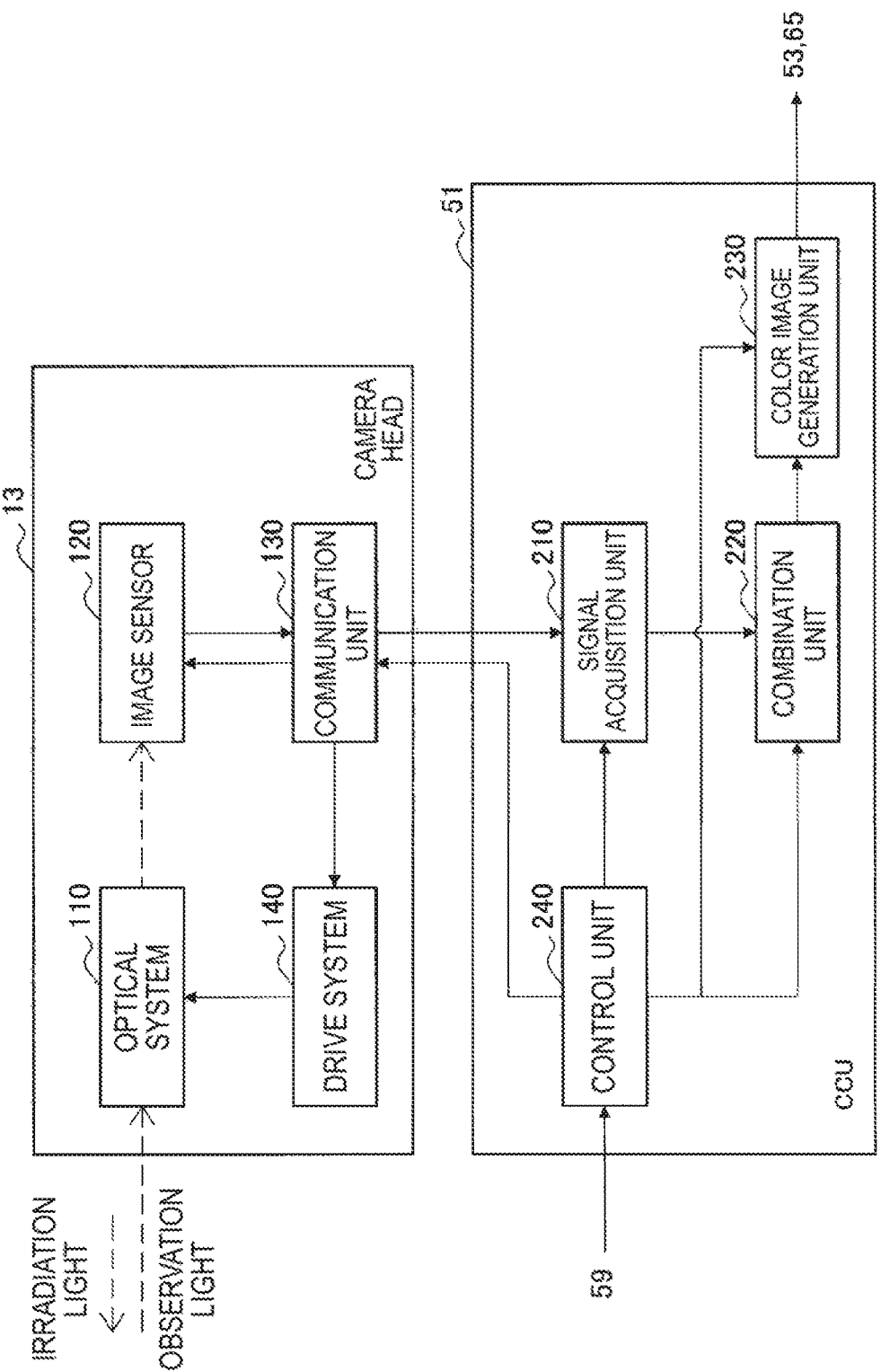
FIG. 2 is a block diagram illustrating an example of configurations of an imaging device (camera head) and an image processing device (CCU) according to an embodiment.

FIG. 2 illustrates an example of a configuration of the camera head 13 serving as an imaging device. When referring to FIG. 2, the camera head 13 includes an optical system 110, an image sensor 120, a communication unit 130, and a drive system 140.

The optical system 110 typically includes a pair of lenses (also referred to as "lens unit") and collects observation light (reflected light of irradiation light) from a subject, the observation light being taken in through the tip of the lens barrel 11, toward the image sensor 120. The lens unit of the optical system 110 can include, for example, a zoom lens and a focus lens. Positions of the zoom lens and the focus lens are changeable by being driven by the drive system 140 in order to variably control imaging conditions such as a magnification and a focus position.

The image sensor 120 performs photoelectric conversion on the observation light collected by the optical system 110 and generates an image signal serving as an electric signal. The image sensor 120 may be a 3CCD sensor including individual imaging elements that generate image signals of respective three color components or may be another type of image sensor such as a 1CCD image sensor or a 2CCD image sensor. The imaging element of the image sensor 120 may be, for example, a complementary metal oxide semiconductor (CMOS), a charge-coupled device CCD), or the like. In an embodiment, the image sensor 120 generates at least an image signal having a single specific color component (hereinafter, "specific component image signal") and two image signals having non-specific color components (hereinafter, "non-specific component image signals") at each frame timing. Then, the image sensor 120 outputs those generated image signals to the communication unit 130.

The communication unit 130 is a communication interface connected to the CCU 51 via a signal line. The signal line between the communication unit 130 and the CCU 51 is, for example, a high-speed transmission line capable of enabling bidirectional communication, such as an optical cable. For example, the communication unit 130 transmits the above-mentioned image signals input from the image sensor 120 to the CCU 51. Further, when a control signal is received from the CCU 51, the communication unit 130 outputs the received control signal to the image sensor 120 or the drive system 140.

The drive system 140 includes an actuator and a controller. The actuator moves a movable member such as the zoom lens or focus lens included in the optical system 110 under the control of the controller that interprets a control signal from the CCU 51. The controller determines operation of the actuator in order to, for example, achieve imaging conditions such as a magnification and a focal distance specified by the control signal. Note that the magnification and the focal distance that are set in the drive system 140 or an imaging condition such as a frame rate that is set in the image sensor 120 may be automatically adjusted in the camera head 13 or may be fixedly set in advance, instead of being controlled by the CCU 51.

[2-2. Image Processing Device]

FIG. 2 also illustrates an example of a configuration of the CCU 51 serving as an image processing device. When referring to FIG. 2, the CCU 51 includes a signal acquisition unit 210, a combination unit 220, a color image generation unit 230, and a control unit 240.

The signal acquisition unit 210 can include a communication interface connected to the communication unit 130 of the above-mentioned camera head 13 via a signal line. In an embodiment, the signal acquisition unit 210 acquires a first specific component image signal that is an image signal with a first exposure for a specific color component. Further, the signal acquisition unit 210 also acquires a second specific component image signal that is an image signal with a second exposure for the specific color component. The signal acquisition unit 210 may acquire both the first and second specific component image signals from the camera head 13. Instead of this, the signal acquisition unit 210 may acquire one of the first and second specific component image signals from the camera head 13 and generate the other specific component image signal on the basis of the acquired one specific component image signal. In the present specification, the expression "image signal with an exposure E" can mean not only an image signal that is a result of actual capturing of an image with the exposure E (which is mainly determined on the basis of exposure time and a diaphragm) but also an image signal having an equivalent signal value to that of an image signal that is virtually captured with the exposure E as a result of calculation of the signal value. For example, it is possible to virtually derive a signal value of an image signal with the exposure E (=E/2+E/2) by adding signal values of two image signals that are actually captured with an exposure of E/2.

Further, the signal acquisition unit 210 also acquires two non-specific component image signals that are image signals corresponding to two color components different from the above specific color component. The signal acquisition unit 210 may perform accompanying processing on those acquired image signals, such as resizing for adjusting resolution and synchronization for synchronizing frame timings. The signal acquisition unit 210 outputs the acquired first and second specific component image signals and the two non-specific component image signals to the combination unit 220. Several more detailed examples of such signal acquisition processing in the signal acquisition unit 210 will be further described below.

The combination unit 220 combines the first and second specific component image signals input from the signal acquisition unit 210 by using a combination weight based on an intensity of the specific color component, thereby generating a specific component combination image signal. As described above, the first and second specific component image signals are image signals with different exposures $E_1$ and $E_2$. Herein, the second exposure $E_2$ is higher than the first exposure $E_1$ ($E_2 > E_1$). Typically, the combination unit 220 performs setting so that, in a pixel in which the specific color component is weak, a combination weight $W_{RS}$ to be applied to the first specific component image signal has a relatively lower value than that of a combination weight $W_{RL}$ to be applied to the second specific component image signal. Note that $W_{RS} + W_{RL} = 1$ is satisfied. That is, in a pixel in which the specific color component is weak, a higher weight is applied to an image signal with a higher exposure, and therefore a defect of a tone in a low-signal-value region is avoided or reduced. Simultaneously, the combination unit 220 performs setting so that, in a pixel in which the specific color component is strong, the combination weight $W_{RS}$ to be applied to the first specific component image signal has a relatively higher value than that of the combination weight $W_{RL}$ to be applied to the second specific component image signal. That is, in a pixel in which the specific color component is strong, a higher weight is applied to an image signal with a lower exposure, and therefore a defect of a tone in a high-signal-value region (saturation of a signal value) is also avoided or reduced. The combination unit 220 outputs the specific component combination image signal generated as a result of such combination to the color image generation unit 230. Further, the combination unit 220 outputs the two non-specific component image signals input from the signal acquisition unit 210 to the color image generation unit 230 as they are.

The color image generation unit 230 generates a color image signal on the basis of the specific component combination image signal and the two non-specific component image signals input from the combination unit 220. In a case where, for example, a dynamic range of the input specific component combination image signal is larger than dynamic ranges of the non-specific component image signals, the color image generation unit 230 may compress the dynamic range of the specific component combination image signal. Further, the color image generation unit 230 may perform, on each image signal, quality improvement processing that can include, for example, one or more of noise reduction, white balance adjustment, blurring correction, and improvement in resolution. The color image generation unit 230 multiplexes the specific component combination image signal and the two non-specific component image signals that have been subjected to, for example, such various types of image signal processing, thereby generating a color image signal, and outputs the generated color image signal to the display device 53 or the recorder 65.

In an embodiment, the color image generation unit 230 may adjust the specific component combination image signal or the two non-specific component image signals so as to cancel a change in a color tone caused by combination of the first specific component image signal and the second specific component image signal in the combination unit 220. Typically, combination of the first specific component image signal with the exposure $E_1$ and the second specific component image signal with the exposure $E_2$ ($E_2 > E_1$) shifts a peak of the signal value downward in the whole dynamic range. Therefore, in a case where, for example, three color components of observation light have the same level (i.e., white light), a signal level of the specific component combination image signal whose dynamic range has been adjusted indicates a lower value than that of a signal level of the non-specific component image signals, that is, a color tone of a generated image may be changed. In view of this, the color image generation unit 230 performs processing for cancelling such an undesirable change in a color tone, thereby preventing a color tone of a display image from being unnatural. An example of a more detailed configuration of the color image generation unit 230 will be further described below.

The control unit 240 controls operation of the endoscope 10 on the basis of user input detected by the input device 59 and setting information (stored on a storage unit (not illustrated)) so that an image is captured as the user (e.g., the practitioner 3) desires. Further, the control unit 240 controls image processing executed by the signal acquisition unit 210, the combination unit 220, and the color image generation unit 230 described above so that an appropriate image is displayed by the display device 53.

As an example, the control unit 240 may acquire setting information associated with a color component of an observation target and set a specific color component in accordance with the acquired setting information. For example, the setting information may be color component information directly indicating a color component to be mainly observed. Further, the setting information may be surgical operation information or may include an association between surgical operation information and a color component of an observation target defined in advance. For example, in a case where a surgical form indicated by the surgical operation information indicates a normal type of surgical operation, the control unit 240 can set a red (R) component as a specific color component and set a green (G) component and a blue (B) component as non-specific color components. Further, in a case where a surgical form indicated by the setting information indicates surgical operation that needs special light observation, the control unit 240 can set a color component to be mainly observed in an individual surgical form as a specific color component. In the present specification, hereinafter, an example where an image signal of a color image is made up of an R component, a G component, and a B component will be mainly described. However, the technology of the present disclosure is also applicable to a case where an image signal includes another color component.

3. DETAILED EXAMPLES

In this section, more detailed examples of configurations of the units of the above-mentioned CCU 51 will be described. Herein, a specific color component is assumed to be a red (R) component as an example for use in description. However, it should be noted that the following description is also applicable to a case where the specific color component is another color.

[3-1. Acquisition of Image Signal]

Figure 3:
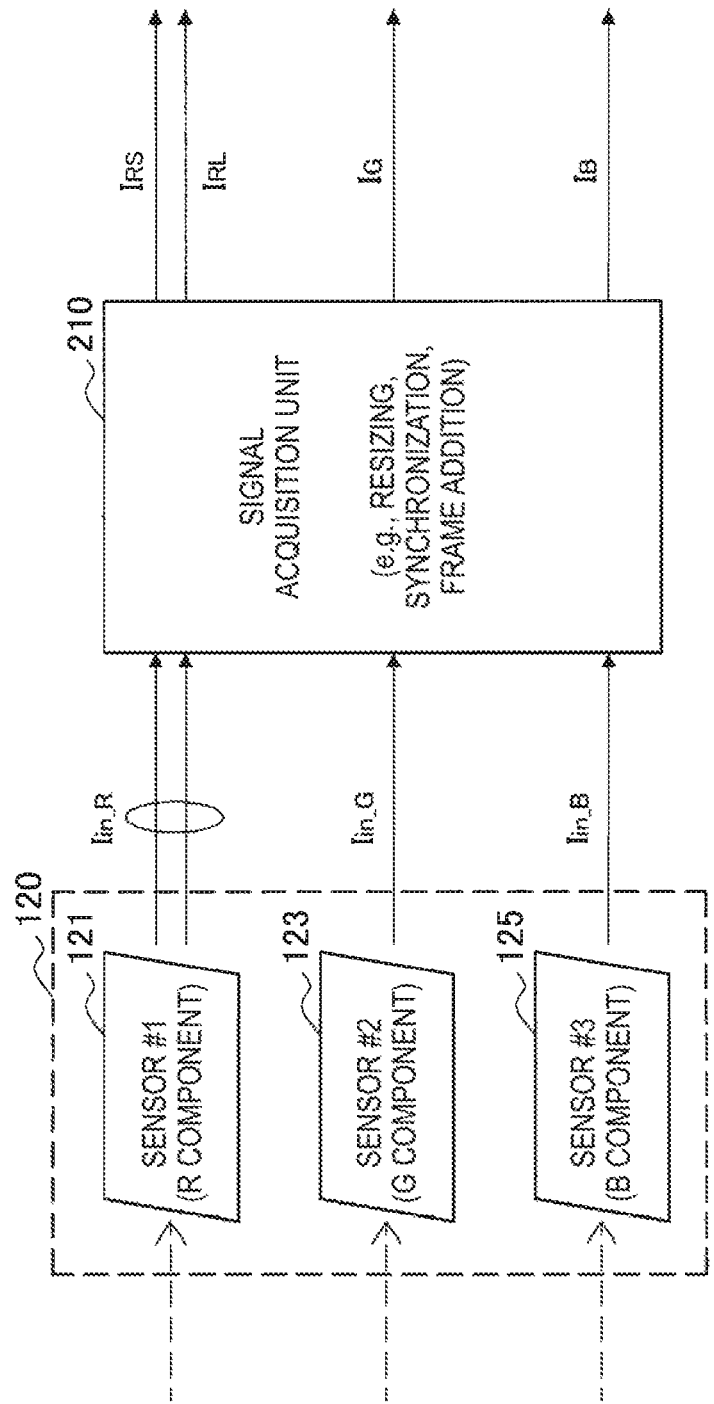
FIG. 3 is an explanatory diagram for schematically describing image signals input to a signal acquisition unit illustrated in FIG. 2 and image signals output from the signal acquisition unit.

FIG. 3 is an explanatory diagram for schematically describing image signals input to the signal acquisition unit 210 illustrated in FIG. 2 and image signals output from the signal acquisition unit 210. FIG. 3 also illustrates an example of a configuration of the image sensor 120 of the camera head 13. Herein, the image sensor 120 is a 3CCD sensor and includes an R component sensor 121, a G component sensor 123, and a B component sensor 125.

At least a single input specific component image signal $I_{in\_R}$ generated by the R component sensor 121 is supplied to the signal acquisition unit 210. For example, the input specific component image signal may include a first specific component image signal $I_{RS}$ with a first exposure and a second specific component image signal $I_{RL}$ with a second exposure. Instead of this, the signal acquisition unit 210 may generate one or both the first specific component image signal $I_{RS}$ and the second specific component image signal $I_{RL}$ from the input specific component image signal. Further, an input non-specific component (G component) image signal $I_{in\_G}$ generated by the G component sensor 123 and an input non-specific component (B component) image signal $I_{in\_B}$ generated by the B component sensor 125 are supplied to the signal acquisition unit 210. Note that, in a case where the image sensor 120 is a 1CCD sensor having a Bayer array, the signal acquisition unit 210 can separate the input image signals of three types of color components by demosaicing the image signals generated by the image sensor 120 before processing described below.

FIGS. 4A to 4D are explanatory diagrams for describing four exemplary methods for acquiring image signals with different exposures.

(1) First Method

According to a first method illustrated in FIG. 4A, the signal acquisition unit 210 acquires a first specific component image signal for a specific color component generated through exposure for a first exposure time, and a second specific component image signal for the specific color component generated through exposure for a second exposure time.

More specifically, the R component sensor 121 includes an aggregation of pixels having a long exposure time (long storage pixels) corresponding to pixel positions hatched with oblique lines and an aggregation of pixels having a short exposure time (short storage pixels) corresponding to pixel positions hatched with dots. The input specific component image signal $I_{in\_R}$ a input to the signal acquisition unit 210 includes pixel values from both the aggregations of the pixels. The signal acquisition unit 210 extracts only signal values of the short storage pixels ($RS_{1a}$, $RS_{1b}$, $RS_{2a}$, $RS_{2a}$, ...) from the input specific component image signal $I_{in\_R}$ and executes resizing and average calculation (e.g., $RS_1=(RS_{1a}+RS_{1b})/2$) as necessary, thereby acquiring a first specific component image signal $I_{RS}$ ($RS_1$, $RS_2$, $RS_3$, $RS_4$, ...). Similarly, the signal acquisition unit 210 extracts only signal values of the long storage pixels ($RL_{1a}$, $RL_{1b}$, $RL_{2a}$, and $RL_{2b}$, ...) from the input specific component image signal $I_{in\_R}$ and executes resizing and average calculation (e.g., $RL_1=(RL_{1a}+RL_{1b})/2$) as necessary, thereby acquiring a second specific component image signal $I_{RL}$ ($RL_1$, $RL_2$, $RL_3$, $RL_4$, ...).

All pixels of the G component sensor 123 and the B component sensor 125 have a uniform exposure time, and the exposure time may be equal to any one of the exposure time of the long storage pixels of the R component sensor 121 and the exposure time of the short storage pixels thereof. The signal acquisition unit 210 executes, for example, resizing and average calculation (e.g., $G_1=(G_{1a}+G_{1b}+G_{1c}+G_{1d})/4$) with respect to a signal value of the input non-specific component image signal $I_{in\_G}$ from the G component sensor 123 so as to solve a difference in resolution between color components, thereby acquiring a first non-specific component image signal $I_G$. Further, the signal acquisition unit 210 similarly executes resizing and average calculation (e.g., $B_1=(B_{1a}+B_{1b}+B_{1c}+B_{1d})/4$) with respect to a signal value of the input non-specific component image signal $I_{in\_B}$ from the B component sensor 125, thereby acquiring a second non-specific component image signal $I_B$. Although such resizing may slightly reduce resolution of an image, such reduction in resolution does not influence practicability of the image because image sensors that have been used in recent years have sufficiently high resolution.

In the example of FIG. 4A, the pixel group having a long exposure time and the pixel group having a short exposure time are spatially alternately arranged in the R component sensor 121. However, those pixel groups may be arranged in another spatial pattern.

Note that, in the R component sensor 121, exposure for two types of exposure time by a time division method and capturing of an image may be performed instead of spatially dispersing the pixel groups exposed for two types of exposure time. In this case, the pixel groups of the R component sensor 121 are exposed for the first exposure time at a first timing and are exposed for the second exposure time at a second timing. Then, the signal acquisition unit 210 can acquire a first specific component image signal from the R component sensor 121 at the first timing and acquire a second specific component image signal from the R component sensor 121 at the second timing.

(2) Second Method

Figure 4B:
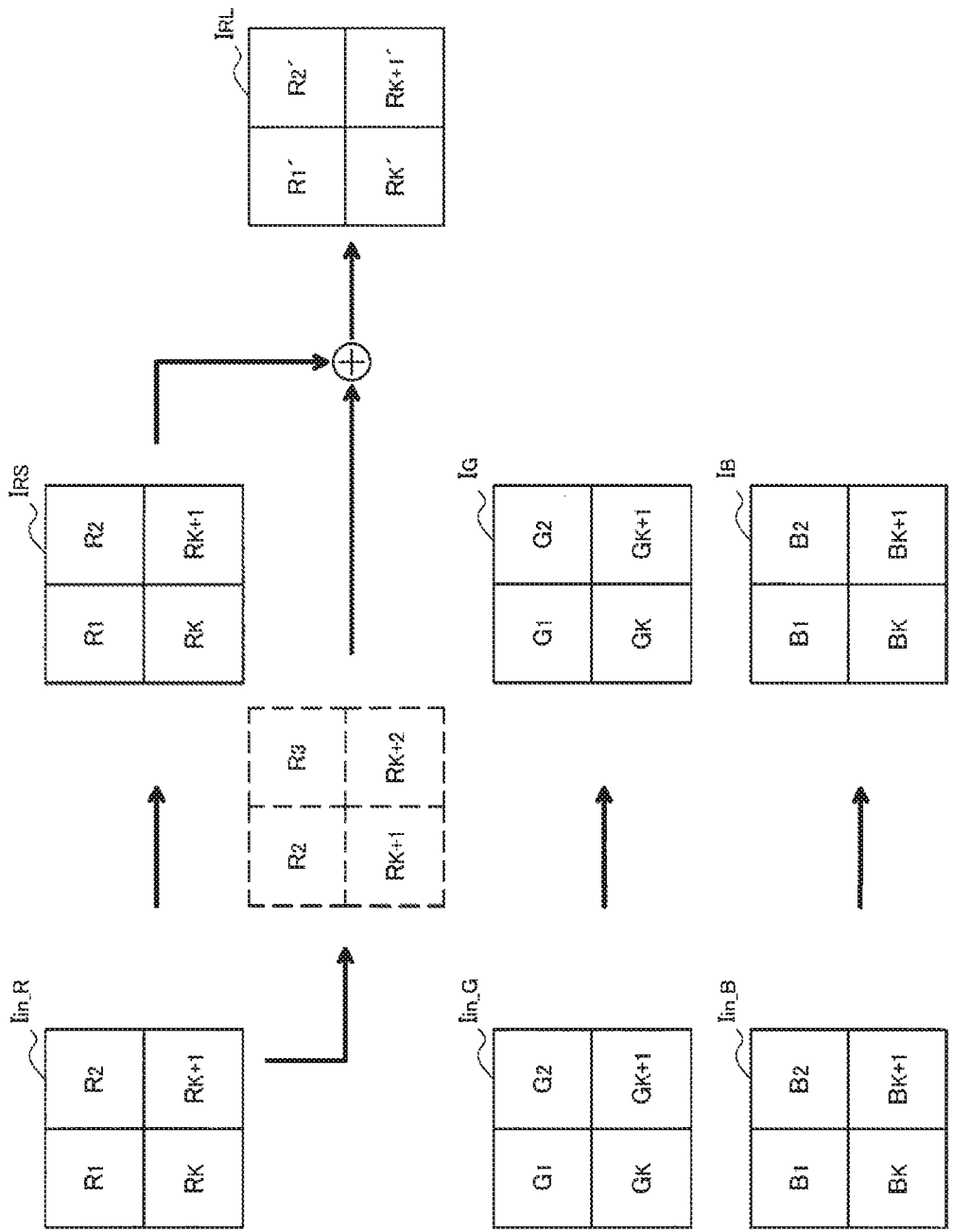
FIG. 4B is an explanatory diagram for describing a second method for acquiring image signals with different exposures.

According to a second method illustrated in FIG. 4B, the signal acquisition unit 210 acquires a first specific component image signal for a specific color component from a pixel group exposed for a first exposure time and acquires a second specific component image signal by adding signal values of adjacent pixels in the first specific component image signal.

In the second method, all pixels of the R component sensor 121, the G component sensor 123, and the B component sensor 125 may have a uniform exposure time. The input specific component image signal $I_{in\_R}$ input to the signal acquisition unit 210 is treated as it is as a first specific component image signal $I_{RS}$ ($R_1$, $R_2$, ..., $R_K$, $R_{K+1}$, ...). Further, the signal acquisition unit 210 adds signal values at respective pixel positions in the input specific component image signal $I_{in\_R}$ to signal values s ($R_2$, $R_3$, ..., $R_{K+1}$, $R_{K+2}$, ...) at adjacent pixel positions, thereby acquiring a second specific component image signal $I_{RL}$ ($R_1'$, $R^{2t}$, ..., $R_K'$, $R_{K+1}'$, ...). The second specific component image signal $I_{RL}$ is an image signal with a simulatively higher exposure than that of the first specific component image signal $I_{RS}$.

As illustrated in FIG. 4B, the signal acquisition unit 210 may treat the first input non-specific component image signal $I_{in\_G}$ and the second input non-specific component image signal $I_{in\_B}$ as the first non-specific component image signal $I_G$ and the second non-specific component image signal $I_B$ as they are. Instead of this, the signal acquisition unit 210 may add signal values of adjacent pixels also in the non-specific component image signals, thereby generating non-specific component image signals with a simulatively higher exposure.

(3) Third Method

Figure 4C:
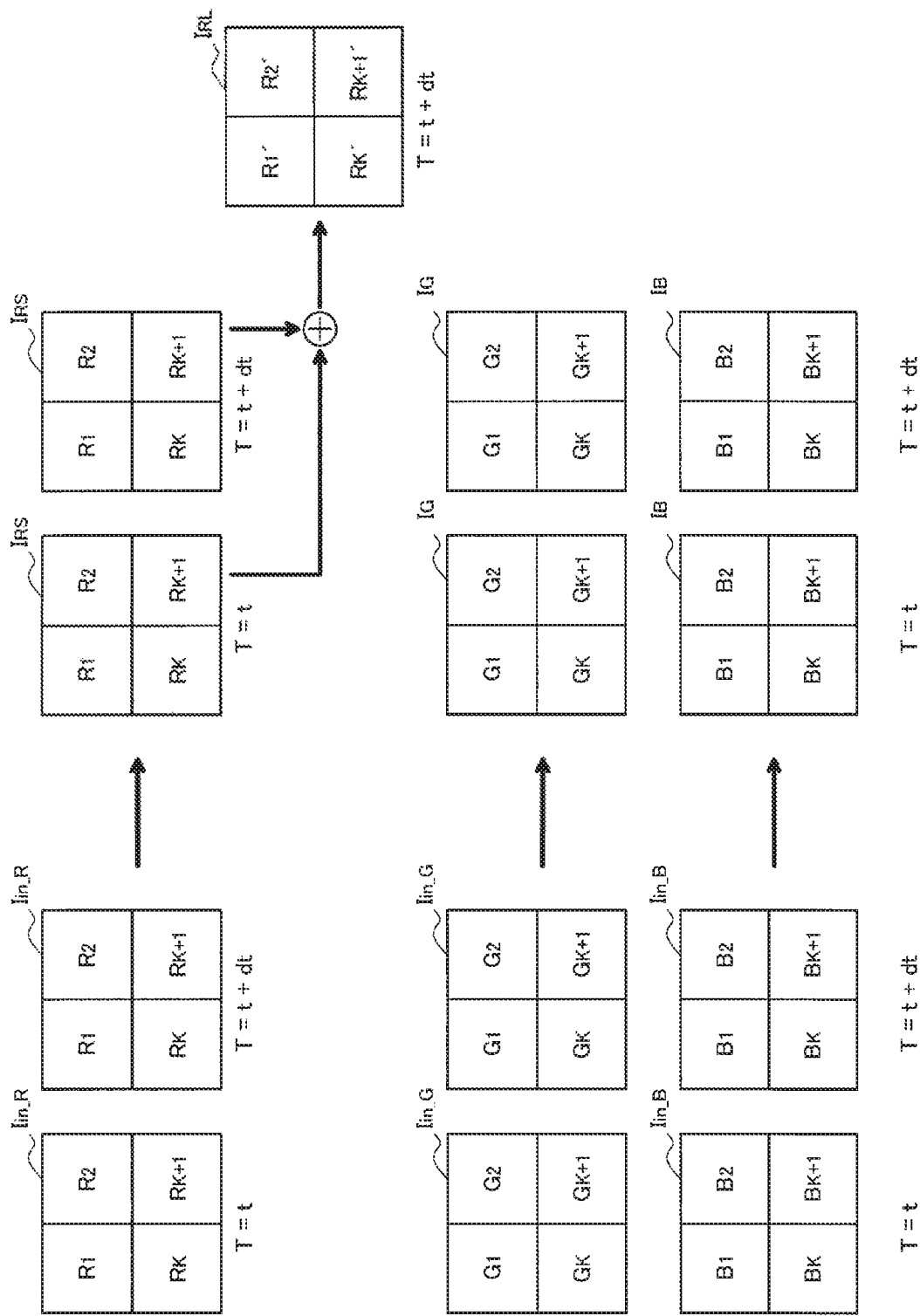
FIG. 4C is an explanatory diagram for describing a third method for acquiring image signals with different exposures.

According to a third method illustrated in FIG. 4C, the signal acquisition unit 210 acquires, at a first frame rate, a first specific component image signal from a pixel group exposed for a first exposure time for a specific color component and adds signal values of first specific component image signals in a plurality of frames that are successive in time, thereby acquiring a second specific component image signal.

In the third method, all pixels of the R component sensor 121, the G component sensor 123, and the B component sensor 125 may have a uniform exposure time. The input specific component image signal input to the signal acquisition unit 210 is treated as it is as a first specific component image signal $I_{RS}$ ($R_1, R_2, \ldots, R_K, R_{K+1}, \ldots$). Further, the signal acquisition unit 210 adds a signal value of the input specific component image signal $I_{in\_R}$ acquired at a time T=t and a signal value of the input specific component image signal $I_{in\_R}$ acquired at a time T=t+dt (dt is a reciprocal of the frame rate) at each common pixel position, thereby acquiring a second specific component image signal $I_{RL}$ ($R_1', R_2', \ldots, R_K', R_{K+1}', \ldots$). The second specific component image signal $I_{RL}$ is an image signal with a substantially higher exposure than that of the first specific component image signal $I_{RS}$.

Note that the second specific component image signal $I_{RL}$ may be generated at a second frame rate that is equal to half of the first frame rate (e.g., in a case where the first frame rate is $F_1$=120 [frames/sec], the second frame rate is $F_2$=60 [frames/sec]). Instead of this, the second specific component image signal $I_{RL}$ may be acquired at a rate equal to the first frame rate (i.e., $F_1=F_2$) by adding, for example, the Kth and K+1th frames and then adding the K+1th and K+2th frames.

As illustrated in FIG. 4C, the signal acquisition unit 210 may treat the first input non-specific component image signal $I_{in\_G}$ and the second input non-specific component image signal $I_{in\_B}$ as the first non-specific component image signal $I_G$ and the second non-specific component image signal $I_B$ as they are. Instead of this, the signal acquisition unit 210 may add signal values for the input non-specific component image signals in a plurality of frames that are successive in time, thereby generating non-specific component image signals with a higher exposure.

(4) Fourth Method

According to a fourth method illustrated in FIG. 4D, the signal acquisition unit 210 acquires a first specific component image signal and a second specific component image signal from an imaging device including a pixel group that receives light of a specific color component through a filter having a first transmittance and a pixel group that receives the light of the specific color component through a filter having a transmittance different from the first transmittance.

The example of FIG. 4D illustrates, for an R component, an input specific component image signal based on light passed through a filter 122 having a relatively high transmittance and an input specific component image signal $I_{in\_RS}$ based on light passed through a filter 124 having a relatively low transmittance. Also in the fourth method, all the pixels of the R component sensor 121, the G component sensor 123, and the B component sensor 125 may have a uniform exposure time. For example, the signal acquisition unit 210 treats the input specific component image signal $I_{in\_RS}$ as the first specific component image signal $I_{RS}$ ($RS_1$, $RS_2$, $RS_3$, $RS_4$, . . . ) and treats the input specific component image signal $I_{in\_RL}$ as the second specific component image signal $I_{RL}$ ($RL_1$, $RL_2$, $RL_3$, $RL_4$, . . . ). Note that pixels for the two input specific component image signals $I_{in\_RS}$ and $I_{in\_RL}$ may coexist in the single R component sensor 121 as described with reference to FIG. 4A or may be arranged in different sensors. In the latter case, the filter 122 is attached to one sensor, and the filter 124 is attached to the other sensor.

Further, the signal acquisition unit 210 treats the input specific component image signal $I_{in\_G}$ based on light passed through a filter 126 as the first non-specific component image signal $I_G$ and treats the input specific component image signal $I_{in\_B}$ based on light passed through a filter 128 as the second non-specific component image signal $I_B$. Transmittances of the filters 126 and 128 may be equal to the (relatively low) transmittance of the filter 124 or may be equal to the (relatively high) transmittance of the filter 122 as illustrated in FIG. 4D. Further, one of the filters 122 and 124, the filter 126, and the filter 128 may be omitted from the configuration of the image sensor 120.

The signal acquisition unit 210 outputs the four types of image signals acquired in any one of the methods described in this section, i.e., the first specific component image signal $I_{RS}$, the second specific component image signal $I_{RL}$, the first non-specific component image signal $T_G$, and the second non-specific component image signal $I_B$ to the combination unit 220.

[3-2. Generation of Specific Component Combination Image Signal]

Figure 5:
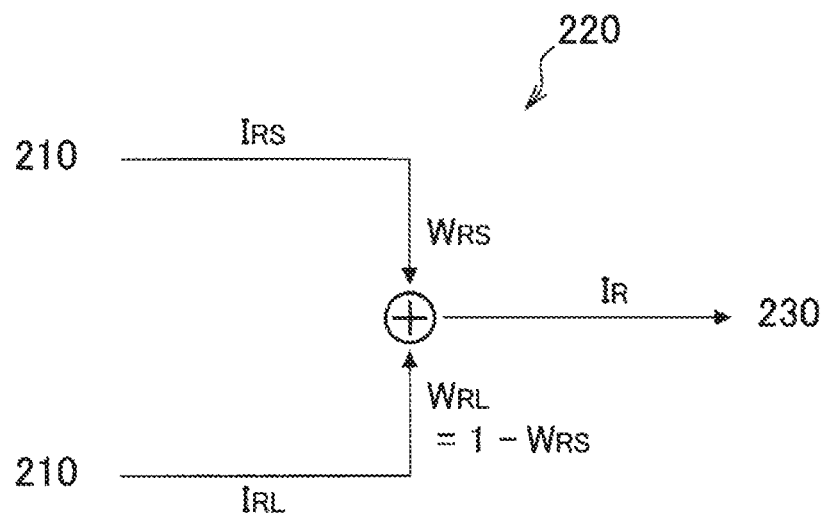
FIG. 5 is an explanatory diagram for describing combination of signals in a combination unit illustrated in FIG. 2.

Next, combination of signals in the combination unit 220 will be described again with reference to FIGS. 5 and 6. An arrow appearing from the left in an upper part of FIG. 5 indicates the first specific component image signal $I_{RS}$, and an arrow appearing from the left in a lower part thereof indicates the second specific component image signal $I_{RL}$. The combination unit 220 applies the combination weight $W_{RS}$ to the first specific component image signal $I_{RS}$ and the combination weight $W_{RL}$ to the second specific component image signal $I_{RL}$. A sum of the combination weight $W_{RS}$ and the combination weight $W_{RL}$ is equal to 1, and both the combination weights $W_{RS}$ and $W_{RL}$ are real numbers of zero or more but 1 or less. Values of the combination weights $W_{RS}$ and $W_{RL}$ are variable, and the combination unit 220 determines the values of those weights for each pixel depending on signal values of the specific component signals (i.e., the intensity of the specific color component).

Figure 6:
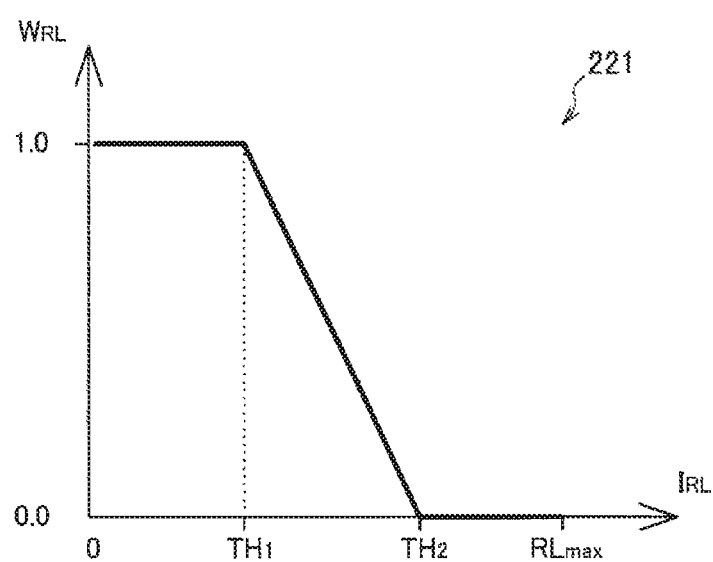
FIG. 6 is a graph showing an example of a relationship between a signal value of a specific component image signal and a combination weight.

FIG. 6 is a graph showing an example of a relationship between a signal value of the second specific component image signal $I_{RL}$ and the combination weight $W_{RL}$. According to a graph 221 of FIG. 6, the combination weight $W_{RL}$ is equal to 1.0 in a section in which the signal value of the specific component image signal falls below a threshold $TH_1$. The combination weight $W_{RL}$ is uniformly reduced from 1.0 to zero in a section in which the signal value of the specific component image signal is equal to or more than the threshold $TH_1$ and is equal to or less than a threshold $TH_2$. The combination weight $W_{RL}$ is equal to zero in a section in which the signal value of the specific component image signal exceeds the threshold $TH_2$ (to a maximum value $RL_{max}$). In a case where the combination weight is determined as described above, the second specific component image signal $I_{RL}$ contributes more to a combination image signal in an image region in which an R component serving as the specific color component is weak, whereas the first specific component image signal $I_{RS}$ contributes more to the combination image signal in an image region in which the R component is strong. As a result, a defect of a tone of the R component is avoided or reduced in both a low-signal-value region and a high-signal-value region of the combination image signal generated by the combination unit 220. Note that a graph showing a relationship between a signal value and a combination weight is not limited to the example illustrated in FIG. 6, and the graph may have any track as long as the track tends to be reduced as a signal value is increased.

The combination unit 220 outputs the specific component combination image signal $I_R$ generated as described above to the color image generation unit 230.

[3-3. Generation of Color Image]

Figure 7:
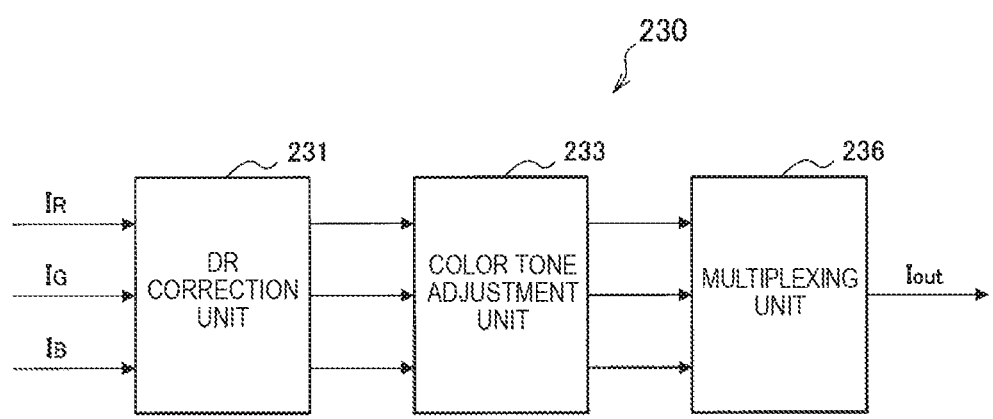
FIG. 7 is a block diagram illustrating an example of a more detailed configuration of a color image generation unit illustrated in FIG. 2.

FIG. 7 illustrates an example of a more detailed configuration of the color image generation unit 230 illustrated in FIG. 2. When referring to FIG. 7, the color image generation unit 230 includes a dynamic range (DR) correction unit 231, a color tone adjustment unit 233, and a multiplexing unit 236.

(1) Correction of Dynamic Range

According to a certain example, among the four types of image signals acquired by the signal acquisition unit 210, only the second specific component image signal $I_{RL}$ is with a higher exposure than exposures of the other image signals including the non-specific component image signals. In this case, a dynamic range of the specific component combination image signal $I_R$ input to the color image generation unit 230 can be larger than dynamic ranges of the two non-specific component image signals $I_G$ and $I_B$. In view of this, the DR correction unit 231 compresses the dynamic range of the specific component combination image signal $I_R$ so that the dynamic ranges of the specific component combination image signal $I_R$, the non-specific component image signal $I_G$, and the non-specific component image signal $I_B$ are equal to one another. More specifically, the DR correction unit 231 multiplies a correction factor less than 1 by the specific component combination image signal $I_R$ and can therefore compress the dynamic range thereof. For example, the DR correction unit 231 may linearly correct a signal value by using a fixed correction factor corresponding to a ratio of widths of the dynamic ranges. Instead of this, the DR correction unit 231 may execute nonlinear correction such as gamma correction.

Figure 8:
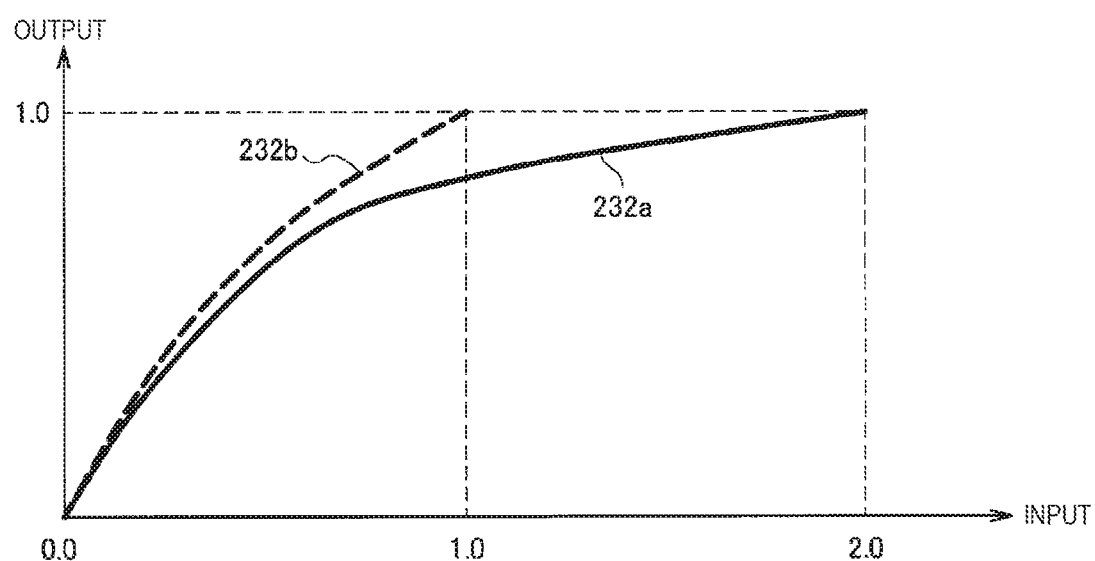
FIG. 8 is a graph showing an example of nonlinear correction for compressing a dynamic range.

FIG. 8 is a graph showing an example of nonlinear correction for compressing a dynamic range. FIG. 8 shows a correction factor curve 232a that can be used when an input value of zero to 2.0 is corrected to an output value of zero to 1.0. The correction factor curve 232a corresponds to a so-called hyper-gamma curve. The DR correction unit 231 performs gamma correction on the specific component combination image signal $I_R$ by using a correction factor having such a curve and can therefore compress the dynamic range of the specific component combination image signal $I_R$ while retaining a tone in the high-signal-value region of the R component more favorably. Meanwhile, a correction factor curve 232b of FIG. 8 is a normal gamma curve that does not change the dynamic range between an input value and an output value. The DR correction unit 231 may also perform gamma correction on the non-specific component image signals $I_G$ and $I_B$ in accordance with the correction factor curve 232b.

Note that, instead of compressing the dynamic range of the specific component combination image signal $I_R$, the DR correction unit 231 may expand the dynamic ranges of the non-specific component image signals $I_G$ and $I_B$ so that the dynamic ranges of the specific component combination image signal $I_R$ and the non-specific component image signals $I_G$ and $I_B$ are equal to one another.

(2) Adjustment of Color Tone

As already described, combination of two specific component image signals with different exposures in the combination unit 220 shifts a peak of a signal value downward in the whole dynamic range of an image signal with a higher exposure. In addition, in a case where only a signal value of a specific color component is reduced, a color tone of a color image that is supposed to be finally obtained may be changed against the intention.

Figure 9A:
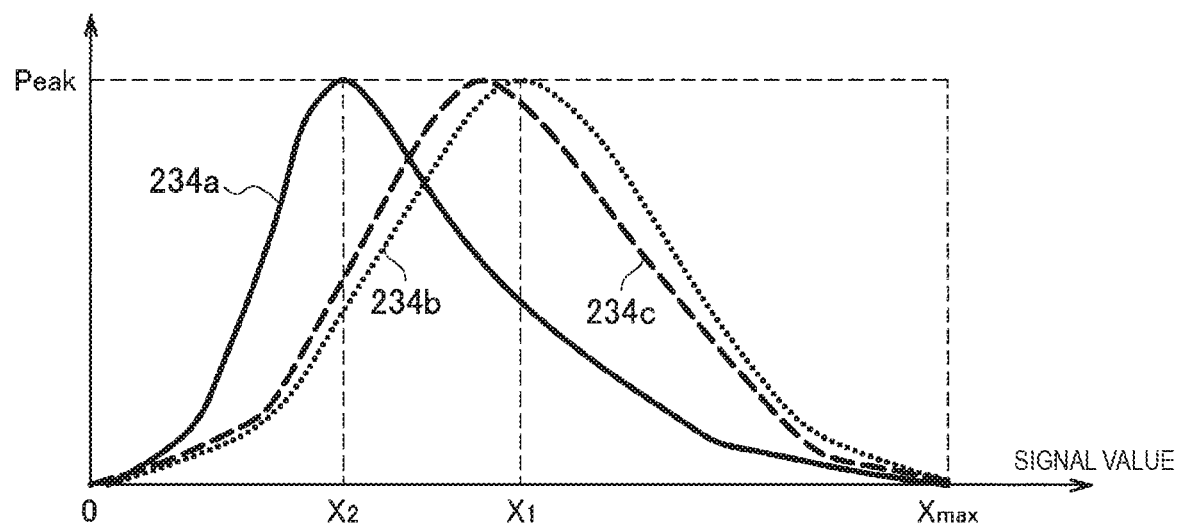
FIG. 9A is an explanatory diagram for describing an example of a change in a color tone caused by combination of two specific component image signals.

FIG. 9A is an explanatory diagram for describing an example of a change in a color tone caused by combination of two specific component image signals. A horizontal axis of FIG. 9A indicates a dynamic range of each color component from zero to a maximum value $X_{max}$. A vertical axis thereof indicates a degree of a signal value. A graph 234a shows a distribution of signal values of the R component, a graph 234b shows a distribution of signal values of the G component, and a graph 234c shows a distribution of signal values of the B component. For example, when a color tone of observation light is close to white and, only for the R component serving as the specific color component, the above-mentioned two specific component image signals with different exposures are combined, only a peak of the signal value of the R component is reduced from, for example, a value $X_1$ to a value $X_2$. Peaks of the signal values of the G component and the B component serving as non-specific color components are maintained in the vicinity of the value $X_1$. When a color image is caused to be displayed as it is without adjusting the color tone, a subject in color close to white may be displayed as if the subject is colored with complementary color of red.

In view of this, the color tone adjustment unit 233 adjusts an image signal of at least a single color component so as to cancel such a change in a color tone. As an example, the color tone adjustment unit 233 applies, to the non-specific component image signals $I_G$ and $I_B$, a tone curve that causes the peaks of the non-specific component image signals $I_B$ and $I_B$ to move in a direction in which the change in the color tone is cancelled.

Figure 9B:
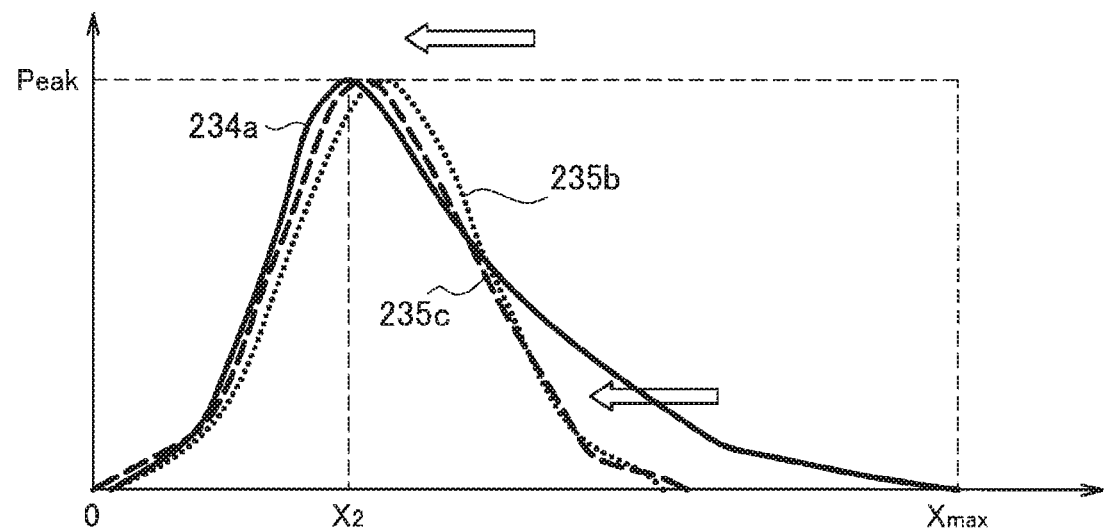
FIG. 9B is an explanatory diagram for describing a distribution of signal values of three color components after a change in a color tone is cancelled.

FIG. 9B shows distributions of the signal values of the three color components after the change in the color tone is cancelled by applying the tone curve to the non-specific component image signals $I_G$ and $I_B$. A graph 235b shows a distribution of the signal values of the G component, and a graph 235c shows a distribution of the signal values of the B component. As understand from FIG. 9B, all the peaks of the signal values of the three color components are positioned in the vicinity of the signal value $X_2$ after the tone curve is applied. When the color image is caused to be displayed on the basis of the image signals adjusted as described above, the subject in color close to white is displayed with color close to white also on a screen. Further, the graph 234a is not changed, i.e., the specific component combination image signal $I_R$ is maintained, and therefore a tone in a high-signal-value region of the R component serving as the specific color component to be observed is favorably maintained.

(3) Multiplexing

The multiplexing unit 236 multiplexes the specific component combination image signal $I_R$ and the two non-specific component image signals $I_G$ and $I_B$ whose color tones have been adjusted by the color tone adjustment unit 233, thereby generating a color image signal and outputs the generated color image signal $I_{out}$ to the display device 53 or the recorder 65.

Although not illustrated in FIG. 7, in order to improve images of individual color components or quality of a color image, the color image generation unit 230 may perform quality improvement processing that can include, for example, one or more of noise reduction, white balance adjustment, blurring correction, and improvement in resolution at an arbitrary timing in the above-mentioned image signal processing.

4. FLOW OF PROCESSING

In this section, examples of a flow of processing that can be executed by the CCU 51 in the above embodiment will be described with reference to several flowcharts. Note that, although a plurality of processing steps are shown in the flowcharts, those processing steps do not necessarily need to be executed in order shown in the flowcharts. Several processing steps may be executed in parallel. Further, an additional processing step may be employed, or part of the processing steps may be omitted.

[4-1. Whole Flow]

FIG. 10 is a flowchart showing an example of a flow of image signal processing according to an embodiment. When referring to FIG. 10, first, the control unit 240 acquires, for example, setting information stored in advance and sets a specific color component in accordance with the acquired setting information (Step S110).

Then, the signal acquisition unit 210 executes signal acquisition processing to acquire a first specific component image signal, a second specific component image signal, and two non-specific component image signals, which are necessary for generating a frame of a color image (Step S120). The first specific component image signal for the specific color component is with a first exposure. The second specific component image signal for the specific color component is with a second exposure different from the first exposure. The two non-specific component image signals for two respective non-specific color components are with the first exposure or the second exposure. Several examples of a more detailed flow of the signal acquisition processing executed herein will be further described below. The signal acquisition unit 210 outputs those acquired image signals to the combination unit 220.

Then, the combination unit 220 combines the first and second specific component image signals input from the signal acquisition unit 210 by using a combination weight based on an intensity of the specific color component, thereby generating a specific component combination image signal (Step S160). In a case where the second exposure is higher than the first exposure, typically, the combination unit 220 sets a combination weight to be applied to the second specific component image signal to be relatively high in a pixel in which the specific color component is weak and sets a combination weight to be applied to the first specific component image signal to be relatively high in a pixel in which the specific color component is strong. Therefore, reproducibility of a tone of the specific color component is increased. Then, the combination unit 220 outputs the specific component combination image signal and the two non-specific component image signals to the color image generation unit 230.

Then, the color image generation unit 230 executes color image generation processing to generate a color image signal on the basis of the specific component combination image signal and the two non-specific component image signals (Step S170). An example of a more detailed flow of the color image generation processing executed herein will be further described below. For example, the color image signal generated by the color image generation unit 230 may be output to the display device 53 in order to display a color image or may be output to the recorder 65 in order to record an image or a moving image.

Steps S120 to S170 described above are repeated until a termination condition of the image signal processing is satisfied (Step S190). For example, when user input to give an instruction to terminate the processing is detected via the input device 59, the above image signal processing is terminated.

[4-2. Signal Acquisition Processing]

(1) First Example

Figure 11A:
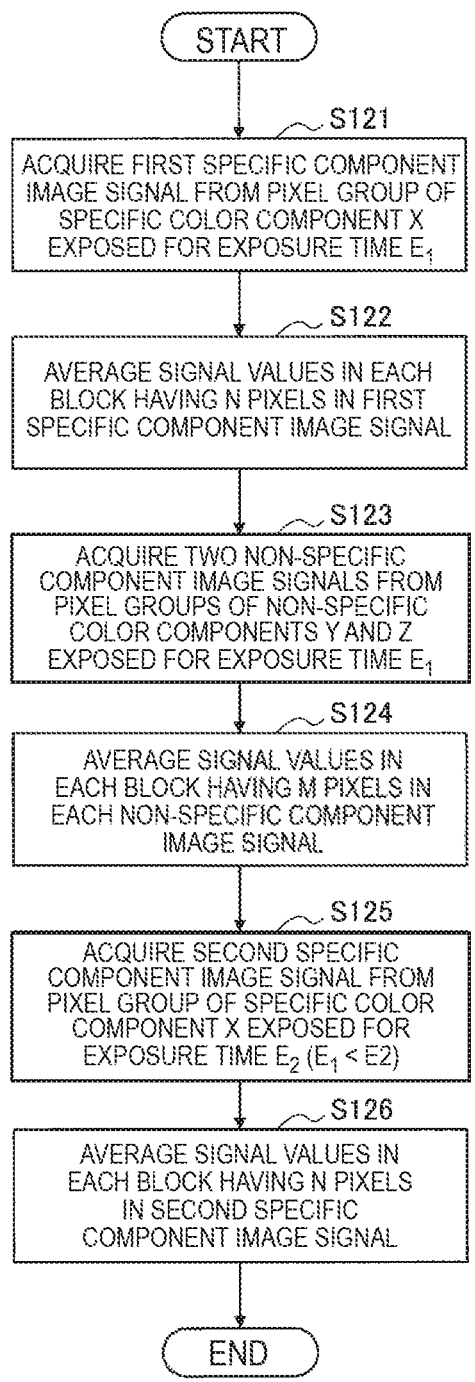
FIG. 11A is a flowchart showing a first example of a more detailed flow of signal acquisition processing.

FIG. 11A is a flowchart showing a first example of the more detailed flow of the signal acquisition processing shown in FIG. 10. The first example corresponds to a scenario described with reference to FIG. 4A.

When referring to FIG. 11A, first, the signal acquisition unit 210 acquires a first specific component image signal from a pixel group of a specific color component X (e.g., X is one of R, G, and B) exposed for an exposure time $E_1$ in the image sensor 120 (Step S121). Then, the signal acquisition unit 210 averages signal values in each block having N pixels in the first specific component image signal (Step S122). According to the example of FIG. 4A, N=2 is satisfied, and N may be an arbitrary integer.

Further, the signal acquisition unit 210 acquires two non-specific component image signals from pixel groups of corresponding non-specific color components Y and Z (e.g., Y and Z are remaining two of R, G, and B) exposed for the exposure time $E_1$ in the image sensor 120 (Step S123). Then, the signal acquisition unit 210 averages signal values in each block having M pixels in each non-specific component image signal (Step S124). According to the example of FIG. 4A, M=4 is satisfied, and M may be an arbitrary integer.

Then, the signal acquisition unit 210 acquires a second specific component image signal from the pixel group of the specific color component X exposed for an exposure time $E_2$ in the image sensor 120 (Step S125). Then, the signal acquisition unit 210 averages signal values in each block having N pixels in the second specific component image signal (Step S126).

(2) Second Example

Figure 11B:
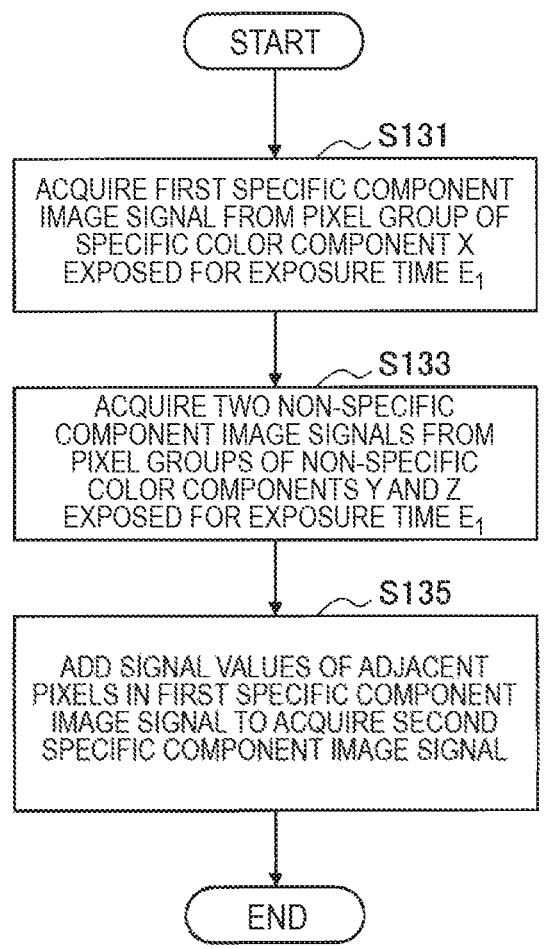
FIG. 11B is a flowchart showing a second example of a more detailed flow of signal acquisition processing.

FIG. 11B is a flowchart showing a second example of the more detailed flow of the signal acquisition processing shown in FIG. 10. The second example corresponds to a scenario described with reference to FIG. 4B.

When referring to FIG. 11B, first, the signal acquisition unit 210 acquires a first specific component image signal from a pixel group of a specific color component X exposed for an exposure time $E_1$ in the image sensor 120 (Step S131).

Further, the signal acquisition unit 210 acquires two non-specific component image signals from pixel groups of corresponding non-specific color components Y and Z exposed for the exposure time $E_1$ in the image sensor 120 (Step S133).

Then, the signal acquisition unit 210 adds signal values of adjacent pixels in the first specific component image signal to acquire a second specific component image signal (Step S135).

(3) Third Example

FIG. 1 IC is a flowchart showing a third example of the more detailed flow of the signal acquisition processing shown in FIG. 10. The third example corresponds to a scenario described with reference to FIG. 4C.

When referring to FIG. 11C, first, the signal acquisition unit 210 acquires a first specific component image signal for the specific color component X in the i-th frame from the image sensor 120 (Step S141).

Further, the signal acquisition unit 210 acquires two corresponding non-specific component image signals for the non-specific color components Y and Z in the i-th frame from the image sensor 120 (Step S143).

Then, the signal acquisition unit 210 acquires a first specific component image signal for the specific color component X in the i+1-th frame from the image sensor 120 (Step S145).

Further, the signal acquisition unit 210 acquires two corresponding non-specific component image signals for the non-specific color components Y and Z in the i+1-th frame from the image sensor 120 (Step S147).

Then, the signal acquisition unit 210 adds, for each pixel, signal values of the first specific component image signals in the i-th and i+1-th frames that are successive in time to acquire a second specific component image signal for the specific color component X (Step S149).

(4) Fourth Example

Figure 11D:
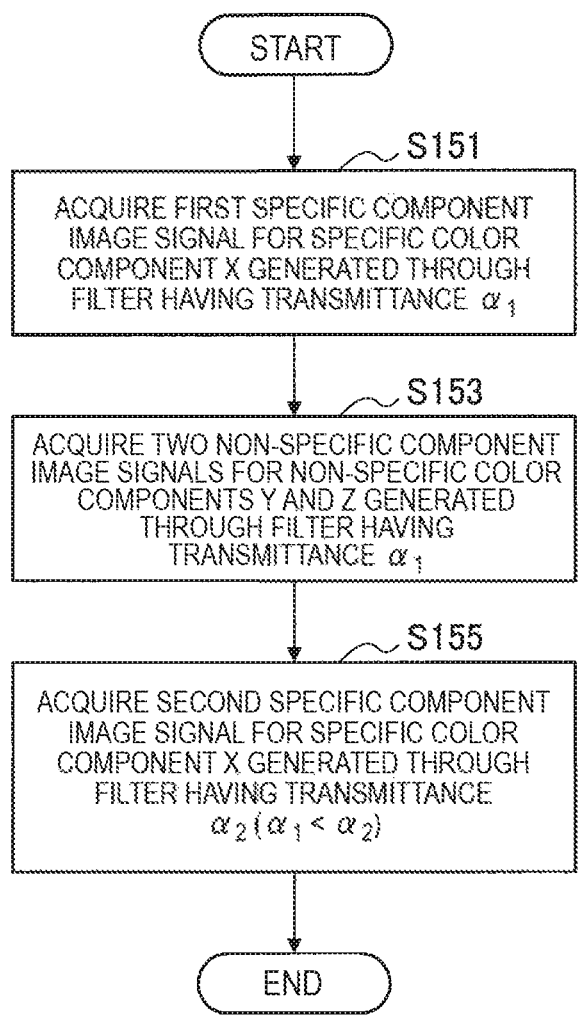
FIG. 11D is a flowchart showing a fourth example of a more detailed flow of signal acquisition processing.

FIG. 11D is a flowchart showing a fourth example of the more detailed flow of the signal acquisition processing shown in FIG. 10. The fourth example corresponds to a scenario described with reference to FIG. 4D.

When referring to FIG. 11D, first, the signal acquisition unit 210 acquires a first specific component image signal for a specific color component X generated through a filter having a transmittance $\alpha_1$ in the image sensor 120 (Step S151).

Further, the signal acquisition unit 210 acquires two non-specific component image signals corresponding to non-specific color components Y and Z generated through the filter having the transmittance $\alpha_1$ in the image sensor 120 (Step S153).

Further, the signal acquisition unit 210 acquires a second specific component image signal for the specific color component X generated through a filter having a transmittance $\alpha_2$ (e.g., $\alpha_1 < \alpha_2$) in the image sensor 120 (Step S155).

[4-3. Color Image Generation Processing]

Figure 12:
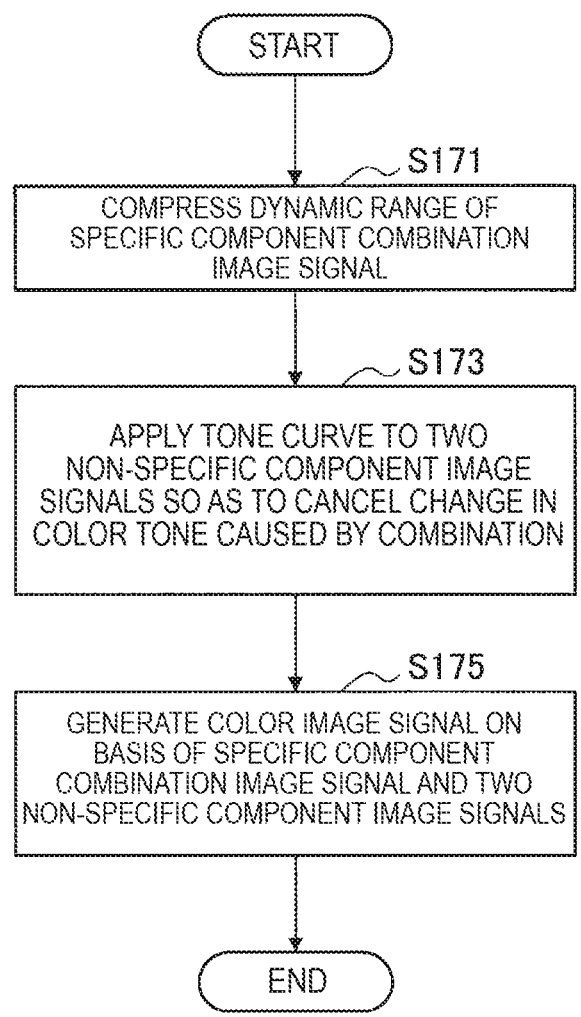
FIG. 12 is a flowchart showing an example of a more detailed flow of color image generation processing.

FIG. 12 is a flowchart showing an example of the more detailed flow of the color image generation processing shown in FIG. 10.

When referring to FIG. 12, first, the color image generation unit 230 compresses a dynamic range of a specific component combination image signal so that the dynamic range of the specific component combination image signal and dynamic ranges of two non-specific component image signals are equal to each other (Step S171).

Then, in order to cancel a change in a color tone caused by combination of the two specific component image signals with different exposures, the color image generation unit 230 applies, to the two non-specific component image signals, a tone curve that causes peaks of the signals to move in a direction in which the change in the color tone is cancelled (Step S173).

Then, the color image generation unit 230 generates a color image signal on the basis of the specific component combination image signal and the two non-specific component image signals that have been subjected to color tone adjustment in the color tone adjustment unit 233 (Step S175).

Note that, although not shown in FIG. 12, the color image generation unit 230 may perform some quality improvement processing such as, for example, noise reduction, white balance adjustment, blurring correction, or improvement in resolution at an arbitrary timing in the color image generation processing.

5. CONTRAST SENSITIVITY OF SIGHT OF HUMAN BEING

Figure 13:
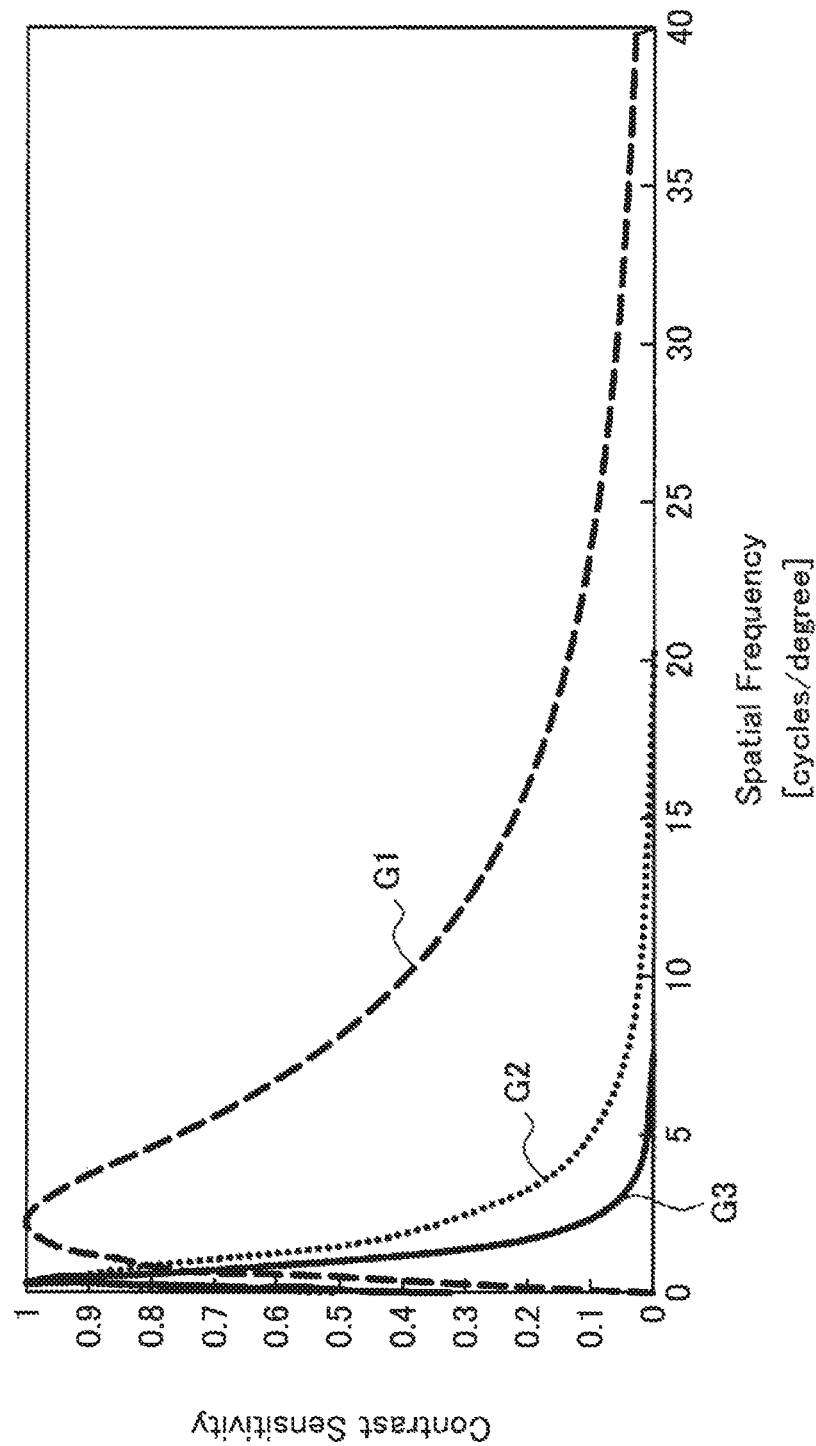
FIG. 13 is a graph showing typical contrast sensitivity of sight of a human being.

FIG. 13 is a graph showing typical contrast sensitivity of sight of a human being. A horizontal axis of FIG. 13 indicates a spatial frequency of texture appearing in a visual field. A vertical axis thereof indicates magnitude of the contrast sensitivity normalized in a range of zero to 1. A graph G1 is an example of a contrast sensitivity function (CSF) curve showing contrast sensitivity of sight of a human being to luminance. A graph G2 is an example of a CSF curve in a red-green region. A graph G3 is an example of a CSF curve in a yellow-blue region. As understood from FIG. 13, peaks of contrast sensitivity of specific color components in sight of a human being are significantly shifted on a lower band side than a band side on which the peak of the contrast sensitivity to luminance is positioned. Therefore, in a case where only a specific color component is subjected to, for example, HDR rendering, subjective degradation in image quality (e.g., reduction in a sense of resolution) sensed by the user is smaller, as compared to a case where three color components are uniformly subjected to similar processing. Also in this point of view, the above-mentioned embodiment in which a specific color component to be observed is particularly set as a target and a tone thereof is maintained or emphasized is advantageous, as compared to an existing method in which three color components are uniformly treated.

6. CONCLUSION

Hereinabove, the embodiment of the technology of the present disclosure has been described in detail with reference to FIGS. 1 to 13. According to the above-mentioned embodiment, a first specific component image signal for a specific color component with a first exposure and a second specific component image signal therefor with a second exposure different from the first exposure are combined by using a weight based on an intensity of the specific color component, and a color image signal is generated on the basis of a specific component combination image signal generated as a result of the combination and two non-specific component image signals. This makes it possible to appropriately adjust a dynamic range of the specific color component corresponding to a color component that strongly influences a tone of a subject or a color component that is particularly meaningful in the tone of the subject and effectively reduce a risk that a tone to be observed is defective.

Further, according to the above-mentioned embodiment, the color image signal may be generated after the image signals are adjusted to cancel a change in a color tone caused by combination of the first specific component image signal and the second specific component image signal. This makes it possible to prevent an undesirable change in the color tone caused by adjustment of the signals only for the specific color component from appearing in a color image that is finally output.

Further, according to the above-mentioned embodiment, in order to cancel the change in the color tone, a tone curve that causes peaks of the non-specific component image signals to move may be applied to the non-specific component image signals. This makes it possible to favorably maintain, for example, a tone in a high-signal-value region of the specific color component while preventing the undesirable change in the color tone.

Further, according to a certain example, the first specific component image signal may be generated through exposure for a first exposure time or through a filter having a first transmittance, and the second specific component image signal can be generated through exposure for a second exposure time or through a filter having a second transmittance. In this case, it is possible to maintain or emphasize the tone of the specific color component, without causing motion blur caused by movement of the subject to occur in the specific component combination image signal or losing a sense of resolution.

Further, according to a certain example, the first specific component image signal is acquired from a pixel group exposed for a first exposure time, and the second specific component image signal is generated by adding signal values of adjacent pixels in the first specific component image signal. In this case, it is possible to acquire the second specific component image signal with a simulatively higher exposure than the exposure of the first specific component image signal, without requiring a special configuration or control for treating two exposures in an imaging device.

Further, according to a certain example, the specific color component may be set in accordance with setting information that is dynamically acquired. This makes it possible to dynamically set various color components, such as red color in normal surgical operation and specific color in special light observation, as the specific color component, and it is possible to flexibly adjust the dynamic range of the specific color component that is different in each scene in which a system is used.

Note that examples of the image processing system including a surgical endoscope have been mainly described in the present specification. However, the technology according to the present disclosure is not limited to such examples and is also applicable to other types of endoscopes such as a capsule endoscope or other types of medical observation devices such as a microscope. Further, the technology according to the present disclosure may be achieved as an image processing module (e.g., image processing chip) or camera module to be mounted on such medical observation devices.

The image processing described in the present specification may be achieved by using any one of software, hardware, and a combination of software and hardware. Programs forming software are stored in advance on, for example, a storage medium (non-transitory medium) provided inside or outside each device. In addition, each program is read into a random access memory (RAM) at the time of, for example, execution and is executed by a processor such as a CPU.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according, to the present disclosure may achieve, other effects that are clear to those skilled in the art from the description of this specification.

Additionally, the present technology may also be configured as below.

(1)

A medical image processing device including:

a signal acquisition unit configured to acquire a first specific component image signal with a first exposure for a specific color component, a second specific component image signal with a second exposure different from the first exposure for the specific color component, and two non-specific component image signals corresponding to two color components different from the specific color component;

a combination unit configured to generate a specific component combination image signal by combining the first specific component image signal and the second specific component image signal by using a weight based on an intensity of the specific color component; and a color image generation unit configured to generate a color image signal on a basis of the specific component combination image signal generated by the combination unit and the two non-specific component image signals.

(2)

The medical image processing device according to (1), in which the color image generation unit adjusts the specific component combination image signal or the two non-specific component image signals so as to cancel a change in a color tone caused by the combination of the first specific component image signal and the second specific component image signal.

(3)

The medical image processing device according to (2), in which the color image generation unit adjusts the non-specific component image signals by applying, to the non-specific component image signals, a tone curve that causes peaks of the non-specific component image signals to move in a direction in which the change in the color tone is cancelled.

(4)

The medical image processing device according to any one of (1) to (3), in which the signal acquisition unit acquires the first specific component image signal generated for the specific color component through exposure for a first exposure time and the second specific component image signal generated for the specific color component through exposure for a second exposure time.

(5)

The medical image processing device according to (4), in which the signal acquisition unit acquires the first specific component image signal and the second specific component image signal from an imaging device including both a pixel group exposed for the first exposure time for the specific color component and a pixel group exposed for the second exposure time for the specific color component.

(6)

The medical image processing device according to (4), in which the signal acquisition unit acquires the first specific component image signal and die second specific component image signal from a pixel group for the specific color component, the pixel group being exposed for the first exposure time at a first timing and being exposed for the second exposure time at a second timing.

(7)

The medical image processing device according to any one of (1) to (3), in which the signal acquisition unit acquires die first specific component image signal from a pixel group exposed for a first exposure time for the specific color component and acquires the second specific component image signal by adding signal values of adjacent pixels in the first specific component image signal.

(8)

The medical image processing device according to any one of (1) to (3), in which the signal acquisition unit acquires, at a first frame rate, the first specific component image signal from a pixel group exposed for a first exposure time for the specific color component and acquires the second specific component image signal by adding signal values of the first specific component image signals in a plurality of frames that are successive in time.

(9)

The medical image processing device according to any one of (1) to (3), in which the signal acquisition unit acquires the first specific component image signal and the second specific component image signal from an imaging device including both a pixel group that receives light of the specific color component through a filter having a first transmittance and a pixel group that receives light of the specific color component through a filter having a transmittance different from the first transmittance.

(10)

The medical image processing device according to any one of (1) to (9), in which the second exposure is higher than the first exposure, and the combination unit applies a relatively high combination weight to the second specific component image signal in a pixel in which the specific color component is weak and applies a relatively high combination weight to the first specific component image signal in a pixel in which the specific color component is strong.

(11)

The medical image processing device according to any one of (1) to (10), in which the specific color component is a red component.

(12)

The medical image processing device according to any one of (1) to (10), further including a control unit configured to acquire setting information associated with a color component of an observation target and set the specific color component in accordance with the acquired setting information.

(13)

A medical image processing system including:

an imaging device configured to capture an image of a subject; and an image processing device configured to generate a color image signal by processing one or more image signals acquired from the imaging device, in which the image processing device includes a signal acquisition unit configured to acquire a first specific component image signal with a first exposure for a specific color component, a second specific component image signal with a second exposure different from the first exposure for the specific color component, and two non-specific component image signals corresponding to two color components different from the specific color component, a combination unit configured to generate a specific component combination image signal by combining the first specific component image signal and the second specific component image signal by using a weight based on an intensity of the specific color component, and a color image generation unit configured to generate a color image signal on a basis of the specific component combination image signal generated by the combination unit and the two non-specific component image signals.

(14)

A medical image processing method including:

acquiring a first specific component image signal with a first exposure for a specific color component;

acquiring a second specific component image signal with a second exposure different from the first exposure for the specific color component;

acquiring two non-specific component image signals corresponding to two color components different from the specific color component;

generating a specific component combination image signal by combining the first specific component image signal and the second specific component image signal by using a weight based on an intensity of the specific color component; and generating a color image signal on a basis of the specific component combination image signal generated by the combination and the two non-specific component image signals.

(15)

A program for causing a processor that controls a medical image processing device to function as:

a signal acquisition unit configured to acquire a first specific component image signal with a first exposure for a specific color component, a second specific component image signal with a second exposure different from the first exposure for the specific color component, and two non-specific component image signals corresponding to two color components different from the specific color component;

a combination unit configured to generate a specific component combination image signal by combining the first specific component image signal and the second specific component image signal by using a weight based on an intensity of the specific color component; and a color image generation unit configured to generate a color image signal on a basis of the specific component combination image signal generated by the combination unit and the two non-specific component image signals.

REFERENCE SIGNS LIST 1 medical image processing system
13 camera head (imaging device)
51 CCU (image processing device)
53 monitor (display device)
15 210 signal acquisition unit
220 combination unit
230 color image generation unit
240 control unit

The invention claimed is:

1. A medical image processing device comprising:
circuitry configured to
acquire a first specific component image signal with a first exposure for a first color component, a second specific component image signal with a second exposure different from the first exposure for the first color component, a first non-specific component image signal for a second color component, different from the first color component, and a second non-specific component image signal for a third color component, different from the first and second color components, wherein a total number of exposures for the first color component is greater than that for the second color component and that for the third color component;

generate a specific component combination image signal by combining the first specific component image signal and the second specific component image signal by using a weight based on an intensity of the first color component;

adjust the specific component combination image signal or the first and second non-specific component image signals so as to cancel a change in a color tone caused by the combination of the first specific component image signal and the second specific component image signal; and generate a color image signal on a basis of the adjusted specific component combination image signal and the first and second non-specific component image signals, wherein, before the specific component image signal is adjusted, the first color component affects a tone of the color image signal more than the second and third color components.

2. The medical image processing device according to claim 1, wherein
the circuitry is further configured to adjust the first and second non-specific component image signals by applying, to the first and second non-specific component image signals, a tone curve that causes peaks of the first and second non-specific component image signals to move in a direction in which the change in the color tone is cancelled.

3. The medical image processing device according to claim 1, wherein
the circuitry is further configured to acquire the first specific component image signal generated for the first color component through exposure for a first exposure time and the second specific component image signal generated for the first color component through exposure for a second exposure time.

4. The medical image processing device according to claim 3, wherein
the circuitry is further configured to acquire the first specific component image signal and the second specific component image signal from an imaging device including both a pixel group exposed for the first exposure time for the first color component and a pixel group exposed for the second exposure time for the first color component.

5. The medical image processing device according to claim 3, wherein
the circuitry is further configured to acquire the first specific component image signal and the second specific component image signal from a pixel group for the first color component, the pixel group being exposed for the first exposure time at a first timing and being exposed for the second exposure time at a second timing.

6. The medical image processing device according to claim 1, wherein
the circuitry is further configured to acquire the first specific component image signal from a pixel group exposed for a first exposure time for the first color component and acquires the second specific component image signal by adding signal values of adjacent pixels in the first specific component image signal.

7. The medical image processing device according to claim 1, wherein
the circuitry is further configured to acquire, at a first frame rate, the first specific component image signal from a pixel group exposed for a first exposure time for the first color component and the second specific component image signal by adding signal values of the first specific component image signals in a plurality of frames that are successive in time.

8. The medical image processing device according to claim 1, wherein
the circuitry is further configured to acquire the first specific component image signal and the second specific component image signal from an imaging device including both a pixel group that receives light of the first color component through a filter having a first transmittance and a pixel group that receives light of the first color component through a filter having a second transmittance different from the first transmittance.

9. The medical image processing device according to claim 1, wherein
the second exposure is higher than the first exposure, and
the circuitry is further configured to apply a relatively high combination weight to the second specific component image signal in a pixel in which the first color component is weak and applies a relatively high combination weight to the first specific component image signal in a pixel in which the first color component is strong.

10. The medical image processing device according to claim 1, wherein
the first color component is a red component.

11. The medical image processing device according to claim 1,
wherein the circuitry is further configured to acquire setting information associated with a color component of an observation target and set the first color component in accordance with the acquired setting information.

12. The medical image processing device according to claim 1, wherein
the first exposure for the first color component is longer than the second exposure for the first color component.

13. The medical image processing device according to claim 1, wherein the circuitry is configured to:
generate the first specific component image signal by averaging a first number of pixels from a first pixel group for the first color component;
generate the second specific component image signal by averaging the first number of pixels from a second pixel group for the first color component, different than the first pixel group;
generate the first non-specific component image signal for the second color component, by averaging signal values different from a second number of pixels, different than the first number of pixels, for the second color component; and
generate the second non-specific component image signal for the third color component, by averaging signal values different from the second number of pixels, for the third color component.

14. The medical image processing device according to claim 7, wherein
the circuitry is further configured to acquire, at a first frame rate, the first specific component image signal from a pixel group exposed for a first exposure time for the first color component and acquire, at a second frame rate, the second specific component image signal.

15. The medical image processing device according to claim 14, wherein
the second frame rate is half the first frame rate.

16. The medical image processing device according to claim 8, wherein
the first transmittance is greater than the second transmittance.

17. A medical image processing system comprising:
an image sensor that captures an image of a subject; and
an image processing device configured to generate a color image signal by processing one or more image signals from the image sensor, wherein
the image processing device includes circuitry configured to
acquire a first specific component image signal with a first exposure for a first color component, a second specific component image signal with a second exposure different from the first exposure for the first color component, a first non-specific component image signal for a second color component, different from the first color component, and a second non-specific component image signal for a third color component, different from the first and second color components, wherein a total number of exposures for the first color component is greater than that for the second color component and that for the third color component, each exposure of the first color component being different from other exposures of the first color component,
generate a specific component combination image signal by combining the first specific component image signal and the second specific component image signal by using a weight based on an intensity of the first color component,
adjust the specific component combination image signal or the first and second non-specific component image signals so as to cancel a change in a color tone caused by the combination of the first specific component image signal and the second specific component image signal, and
generate a color image signal on a basis of the adjusted specific component combination image signal and the first and second non-specific component image signals, wherein, before the specific component image signal is adjusted, the first color component affects a tone of the color image signal more than the second and third color components.

18. A medical image processing method comprising:
acquiring a first specific component image signal with a first exposure for a first color component;
acquiring a second specific component image signal with a second exposure different from the first exposure for the first color component;
acquiring a first non-specific component image signal corresponding to a second color component different from the first color component;
acquiring a second non-specific component image signal corresponding to a third color component different from the first and second color components, wherein a total number of exposures for the first color component is greater than that for the second color component and that for the third color component;
generating a specific component combination image signal by combining the first specific component image signal and the second specific component image signal by using a weight based on an intensity of the first color component;
adjusting the specific component combination image signal or the first and second non-specific component image signals so as to cancel a change in a color tone caused by the combination of the first specific component image signal and the second specific component image signal; and
generating a color image signal on a basis of the adjusted specific component combination image signal generated by the combination and the first and second non-specific component image signals, wherein, before adjusting the specific component image signal, wherein the first color component affects a tone of the color image signal more than the second and third color components.

19. A non-transitory computer readable medium having stored thereon a program that, when executed by a computer, causes the computer to execute processing, the processing comprising:
acquiring a first specific component image signal with a first exposure for a first color component,
acquiring a second specific component image signal with a second exposure different from the first exposure for the first color component,
acquiring a first non-specific component image signals corresponding to a second color component different from the first color component;
acquiring a second non-specific component image signal corresponding to a third color component different from the first and second color components wherein a number of exposures for the first color component is greater than that for the second color component and that for the third color component;
generating a specific component combination image signal by combining the first specific component image signal and the second specific component image signal by using a weight based on an intensity of the first color component;
adjusting the specific component combination image signal or the first and second non-specific component image signals so as to cancel a change in a color tone caused by the combination of the first specific component image signal and the second specific component image signal; and
generating a color image signal on a basis of the adjusted specific component combination image signal and the first and second non-specific component image signals, wherein, before adjusting the specific component image signal, wherein the first color component affects a tone of the color image signal more than the second and third color components.

* * * * *